US012788406B2

(12) United States Patent

Schultheis et al.

(10) Patent No.: US 12,788,406 B2
(45) Date of Patent: Nov. 10, 2026

(54) MANIFOLD INTEGRATED HANDLE ASSEMBLY FOR INTRAVASCULAR LITHOTRIPSY DEVICE

(71) Applicant: Boston Scientific Scimed, Inc., Maple Grove, MN (US)

(72) Inventors: Eric Schultheis, San Clemente, CA (US); Alvin Salinas, San Marcos, CA (US); Peter Dahl, Riverside, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 641 days.

(21) Appl. No.: 18/106,801

(22) Filed: Feb. 7, 2023

(65) Prior Publication Data

US 2023/0255635 A1 Aug. 17, 2023

Related U.S. Application Data

(60) Provisional application No. 63/309,867, filed on Feb. 14, 2022.

(51) Int. Cl.
*A61B 17/12* (2006.01)

(52) U.S. Cl.
CPC .. *A61B 17/12136* (2013.01); *A61B 17/12109* (2013.01); *A61B 2017/1205* (2013.01)

(58) Field of Classification Search
CPC ... A61B 17/2202–22029; A61B 17/225–2258;
(Continued)

(56) References Cited

U.S. PATENT DOCUMENTS 4,522,194 A 6/1985 Normann
4,649,924 A 3/1987 Taccardi
(Continued)

FOREIGN PATENT DOCUMENTS

AU 2017205323 A1 7/2018
AU 2022227829 9/2022
(Continued)

OTHER PUBLICATIONS

"Custom Medical Skived Tubing", Duke Extrusion, 2025. https://www.dukeextrusion.com/tubing-options/skived-tubing.
(Continued)

*Primary Examiner* — Elizabeth Houston
*Assistant Examiner* — Jonathan A Hollm
(74) *Attorney, Agent, or Firm* — SEAGER, TUFTE & WICKHEM, LLP

(57) ABSTRACT

A catheter system (100) for treating a vascular lesion (106A) within or adjacent to a vessel wall (108A) of a blood vessel (108) within a body (107) of a patient (109) includes a catheter shaft (210); a handle assembly (228); and a source manifold (236). The handle assembly (228) is coupled to the catheter shaft (210). The handle assembly (228) includes an assembly housing (266). The handle assembly (228) is usable by a user to selectively position the catheter shaft (210) near the vascular lesion (106A). The source manifold (236) is coupled to the assembly housing (266). The source manifold (236) includes a manifold housing (282) having a catheter shaft port (264) that is configured to receive a portion of the catheter shaft (210) so that the catheter shaft (210) is coupled to the manifold housing (282).

21 Claims, 3 Drawing Sheets

(58) Field of Classification Search
CPC . A61B 2017/22021–22028; A61B 2017/2253; A61B 2017/0046–00486; A61B 18/22–26; A61B 2018/2205–266
See application file for complete search history.

(56) References Cited

U.S. PATENT DOCUMENTS 4,669,465 A * 6/1987 Moore ................ A61B 18/245 606/7
4,699,147 A 10/1987 Chilson et al.
4,799,479 A 1/1989 Spears
4,850,351 A 7/1989 Herman
4,913,142 A 4/1990 Kittrell et al.
4,932,954 A 6/1990 Wondrazek et al.
4,955,895 A 9/1990 Suglyama
4,960,108 A 10/1990 Reichel et al.
4,994,059 A 2/1991 Kosa et al.
4,998,930 A 3/1991 Lundahl
5,019,075 A 5/1991 Spears et al.
5,034,010 A 7/1991 Kittrell et al.
5,041,121 A 8/1991 Wondrazek et al.
5,057,106 A 10/1991 Kasevich et al.
5,082,343 A 1/1992 Coult et al.
5,093,877 A 3/1992 Aita et al.
5,104,391 A 4/1992 Ingle
5,104,392 A 4/1992 Kittrell et al.
5,109,452 A 4/1992 Selvin et al.
5,116,227 A 5/1992 Levy
5,126,165 A 6/1992 Akihama et al.
5,152,768 A 10/1992 Bhatta
5,173,049 A 12/1992 Levy
5,176,674 A 1/1993 Hofmann
5,181,921 A 1/1993 Makita et al.
5,188,632 A 2/1993 Goldenberg
5,200,838 A 4/1993 Nudelman
5,269,777 A 12/1993 Doiron
5,290,277 A 3/1994 Vercimak et al.
5,324,282 A 6/1994 Dodick
5,328,472 A 7/1994 Steinke et al.
5,336,184 A 8/1994 Teirstein
5,363,458 A 11/1994 Pan
5,372,138 A 12/1994 Crowley
5,387,225 A 2/1995 Euteneur
5,400,428 A 3/1995 Grace
5,410,797 A 5/1995 Steinke et al.
5,417,689 A 5/1995 Fine
5,422,926 A 6/1995 Smith
5,425,375 A * 6/1995 Chin ........................ A61N 1/40 374/142
5,431,647 A 7/1995 Purcell
5,454,809 A 10/1995 Janssen
5,456,680 A 10/1995 Taylor
5,474,537 A 12/1995 Solar
5,496,311 A * 3/1996 Abele .................. A61B 18/082 606/28
5,509,917 A 4/1996 Cecchetti
5,519,798 A 5/1996 Shahid
5,540,679 A 7/1996 Fram
5,562,657 A 10/1996 Griffin
5,598,494 A 1/1997 Behrmann et al.
5,609,606 A 3/1997 O'Boyle
5,611,807 A 3/1997 O'Boyle
5,637,877 A 6/1997 Sinofsky
5,661,829 A 8/1997 Zheng
5,697,377 A 12/1997 Wittkamph
5,718,241 A 2/1998 Ben-Haim et al.
5,729,583 A 3/1998 Tang
5,764,843 A 6/1998 Macken et al.
5,772,609 A 6/1998 Nguyen et al.
5,824,005 A 10/1998 Motamedi et al.
5,860,974 A 1/1999 Abele
5,891,135 A 4/1999 Jackson et al.
5,906,611 A 5/1999 Dodick et al.
5,944,697 A 8/1999 Benett et al.
6,007,514 A 12/1999 Nita
6,015,404 A 1/2000 Altshuler
6,080,119 A 6/2000 Schwarze et al.
6,123,923 A 9/2000 Unger
6,139,510 A 10/2000 Palermo
6,186,963 B1 2/2001 Schwarze et al.
6,203,537 B1 3/2001 Adrian
6,210,404 B1 4/2001 Shadduck
6,339,470 B1 1/2002 Papademetriou et al.
6,356,575 B1 3/2002 Fukumoto
6,368,318 B1 4/2002 Visuri et al.
6,423,055 B1 7/2002 Farr
6,500,174 B1 12/2002 Maguire et al.
6,514,203 B2 2/2003 Bukshpan
6,514,249 B1 2/2003 Maguire
6,524,251 B2 2/2003 Rabiner et al.
6,538,739 B1 3/2003 Visuri et al.
6,544,218 B1 4/2003 Choi
6,548,010 B1 4/2003 Stivland et al.
6,560,387 B1 5/2003 Hehlen et al.
6,607,502 B1 8/2003 Maguire et al.
6,631,220 B1 10/2003 Liang et al.
6,652,547 B2 11/2003 Rabiner et al.
6,666,834 B2 12/2003 Restle et al.
6,702,781 B1 3/2004 Reifart et al.
6,773,447 B2 8/2004 Laguna
6,824,554 B1 11/2004 Jang
6,849,994 B1 2/2005 White et al.
6,890,317 B2 5/2005 Gerdts et al.
6,947,785 B1 9/2005 Beatty et al.
6,966,890 B2 11/2005 Coyle et al.
6,978,168 B2 12/2005 Beatty et al.
6,990,370 B1 1/2006 Beatty et al.
7,273,470 B2 9/2007 Wantink
7,309,324 B2 12/2007 Hayes et al.
7,367,967 B2 5/2008 Eidenschink
7,470,240 B2 12/2008 Schultheiss et al.
7,539,231 B1 5/2009 Honea et al.
7,569,032 B2 8/2009 Naimark et al.
7,599,588 B2 10/2009 Eberle et al.
7,641,646 B2 1/2010 Kennedy, II
7,691,079 B2 4/2010 Gobel
7,713,260 B2 5/2010 Lessard
7,758,572 B2 7/2010 Weber et al.
7,762,984 B2 7/2010 Kumoyama et al.
7,810,395 B2 10/2010 Zhou
7,850,685 B2 12/2010 Kunis et al.
7,867,178 B2 1/2011 Simnacher
7,909,797 B2 3/2011 Kennedy, II et al.
7,942,850 B2 5/2011 Levit et al.
7,967,781 B2 6/2011 Simpson et al.
7,972,299 B2 7/2011 Carter
7,985,189 B1 7/2011 Ogden et al.
8,021,328 B2 9/2011 Lee
8,029,473 B2 10/2011 Carter
8,043,256 B2 10/2011 Hansen
8,066,732 B2 11/2011 Paul et al.
8,088,121 B2 1/2012 Nishide
8,157,760 B2 4/2012 Criado et al.
8,162,859 B2 4/2012 Schultheiss et al.
8,166,825 B2 5/2012 Zhou
8,192,368 B2 6/2012 Woodruff
8,197,505 B2 6/2012 Hirszowicz et al.
8,246,643 B2 8/2012 Nita
8,267,886 B2 9/2012 Ewing
8,292,913 B2 10/2012 Warnack
8,328,820 B2 12/2012 Diamant
8,364,235 B2 1/2013 Kordis et al.
8,372,034 B2 2/2013 Levit
8,382,738 B2 2/2013 Simpson et al.
8,414,527 B2 4/2013 Mallaby
8,419,613 B2 4/2013 Saadat
8,439,890 B2 5/2013 Beyar
8,556,813 B2 10/2013 Cashman et al.
8,556,851 B2 10/2013 Hirszowicz
8,574,247 B2 11/2013 Adams et al.
8,657,814 B2 2/2014 Werneth
8,709,075 B2 4/2014 Adams et al.
8,728,091 B2 5/2014 Hakala et al.
8,734,424 B2 5/2014 Watanabe

(56) References Cited

U.S. PATENT DOCUMENTS

| | | | |
|---|---|---|---|
| 8,747,416 | B2 | 6/2014 | Hakala et al. |
| 8,784,362 | B2 | 7/2014 | Boutilette |
| 8,834,510 | B2 | 9/2014 | Wilson et al. |
| 8,888,788 | B2 | 11/2014 | Hakala et al. |
| 8,956,371 | B2 | 2/2015 | Hawkins et al. |
| 8,956,374 | B2 | 2/2015 | Hawkins et al. |
| 8,986,339 | B2 | 3/2015 | Warnack |
| 8,992,519 | B2 | 3/2015 | Kim et al. |
| 8,992,817 | B2 | 3/2015 | Stamberg |
| 9,005,216 | B2 | 4/2015 | Hakala et al. |
| 9,011,462 | B2 | 4/2015 | Adams et al. |
| 9,011,463 | B2 | 4/2015 | Adams et al. |
| 9,011,511 | B2 | 4/2015 | Gregorich |
| 9,044,575 | B2 | 6/2015 | Beasley et al. |
| 9,044,618 | B2 | 6/2015 | Hawkins et al. |
| 9,044,619 | B2 | 6/2015 | Hawkins et al. |
| 9,056,185 | B2 | 6/2015 | Fischell et al. |
| 9,072,534 | B2 | 7/2015 | Adams et al. |
| 9,089,669 | B2 | 7/2015 | Haslinger et al. |
| 9,131,949 | B2 | 9/2015 | Coleman et al. |
| 9,138,249 | B2 * | 9/2015 | Adams ............ A61B 17/22022 |
| 9,138,260 | B2 | 9/2015 | Miller et al. |
| 9,180,280 | B2 | 11/2015 | Hawkins et al. |
| 9,220,521 | B2 | 12/2015 | Hawkins et al. |
| 9,237,984 | B2 | 1/2016 | Hawkins et al. |
| 9,254,169 | B2 | 2/2016 | Long et al. |
| 9,282,984 | B2 | 3/2016 | Nita |
| 9,283,359 | B2 | 3/2016 | Pepper |
| 9,289,132 | B2 | 3/2016 | Ghaffari et al. |
| 9,289,224 | B2 | 3/2016 | Adams et al. |
| 9,289,319 | B2 | 3/2016 | Pacetti et al. |
| 9,320,530 | B2 | 4/2016 | Grace |
| 9,333,000 | B2 | 5/2016 | Hakala et al. |
| 9,339,632 | B2 | 5/2016 | Eidenschink et al. |
| 9,364,645 | B2 | 6/2016 | Erikawa |
| 9,375,223 | B2 | 6/2016 | Wallace |
| 9,421,025 | B2 | 8/2016 | Hawkins et al. |
| 9,433,428 | B2 | 9/2016 | Hakala et al. |
| 9,433,745 | B2 | 9/2016 | Cully |
| 9,504,809 | B2 | 11/2016 | Bo |
| 9,510,887 | B2 | 12/2016 | Burnett |
| 9,522,012 | B2 | 12/2016 | Adams |
| 9,554,815 | B2 | 1/2017 | Adams et al. |
| 9,555,267 | B2 | 1/2017 | Ein-gal |
| 9,566,209 | B2 | 2/2017 | Katragadda et al. |
| 9,579,114 | B2 | 2/2017 | Mantell et al. |
| 9,579,492 | B2 | 2/2017 | Simpson |
| 9,585,684 | B2 | 3/2017 | Nita et al. |
| 9,592,328 | B2 | 3/2017 | Jeevanandam |
| 9,603,506 | B2 | 3/2017 | Goldfarb et al. |
| 9,629,567 | B2 | 4/2017 | Porath et al. |
| 9,642,673 | B2 | 5/2017 | Adams |
| 9,662,069 | B2 | 5/2017 | De Graff et al. |
| 9,687,166 | B2 | 6/2017 | Subramaniam |
| 9,700,655 | B2 | 7/2017 | Laudenslager et al. |
| 9,730,715 | B2 | 8/2017 | Adams |
| 9,737,361 | B2 | 8/2017 | Magana |
| 9,764,142 | B2 | 9/2017 | Imran |
| 9,782,570 | B2 | 10/2017 | Hirszowicz |
| 9,814,476 | B2 | 11/2017 | Adams et al. |
| 9,833,348 | B2 | 12/2017 | Jordan et al. |
| 9,839,764 | B2 | 12/2017 | Chouinard |
| 9,861,377 | B2 | 1/2018 | Mantell et al. |
| 9,867,629 | B2 | 1/2018 | Hawkins et al. |
| 9,878,135 | B2 | 1/2018 | Holzapfel et al. |
| 9,894,756 | B2 | 2/2018 | Weinkam et al. |
| 9,901,704 | B2 | 2/2018 | Appling |
| 9,955,946 | B2 | 5/2018 | Miller et al. |
| 9,974,963 | B2 | 5/2018 | Imran |
| 9,974,970 | B2 | 5/2018 | Nuta et al. |
| 9,993,292 | B2 | 6/2018 | Adams et al. |
| 10,039,561 | B2 | 8/2018 | Adams et al. |
| 10,076,384 | B2 | 9/2018 | Kasprzyk |
| 10,086,175 | B2 | 10/2018 | Torres et al. |
| 10,124,153 | B2 | 11/2018 | Feig |
| 10,136,829 | B2 | 11/2018 | Deno et al. |
| 10,149,690 | B2 | 12/2018 | Hawkins et al. |
| 10,159,505 | B2 | 12/2018 | Hakala et al. |
| 10,194,994 | B2 | 2/2019 | Deno et al. |
| 10,201,387 | B2 | 2/2019 | Grace et al. |
| 10,206,698 | B2 | 2/2019 | Hakala et al. |
| 10,226,265 | B2 | 3/2019 | Ku et al. |
| 10,245,410 | B2 | 4/2019 | Aggerholm |
| 10,327,846 | B1 | 6/2019 | Stark et al. |
| 10,328,290 | B2 | 6/2019 | Zhou et al. |
| 10,357,264 | B2 | 7/2019 | Kat-Kuoy |
| 10,405,923 | B2 | 9/2019 | Yu et al. |
| 10,406,031 | B2 | 9/2019 | Thyzel |
| 10,406,318 | B2 | 9/2019 | Williams |
| 10,420,569 | B2 | 9/2019 | Adams |
| 10,439,791 | B2 | 10/2019 | Kalhan |
| 10,441,300 | B2 | 10/2019 | Hawkins |
| 10,449,339 | B2 | 10/2019 | Wilson et al. |
| 10,463,430 | B2 | 11/2019 | Dick |
| 10,478,202 | B2 | 11/2019 | Adams et al. |
| 10,517,620 | B2 | 12/2019 | Adams |
| 10,517,621 | B1 | 12/2019 | Hakala et al. |
| 10,537,287 | B2 | 1/2020 | Braido et al. |
| 10,555,744 | B2 | 2/2020 | Nguyen et al. |
| 10,561,428 | B2 | 2/2020 | Eggert et al. |
| 10,583,277 | B2 | 3/2020 | Rundquist |
| 10,589,073 | B2 | 3/2020 | Mallaby |
| 10,617,850 | B2 | 4/2020 | Tal |
| 10,646,240 | B2 | 5/2020 | Betelia et al. |
| 10,668,245 | B2 | 6/2020 | Kanae |
| 10,682,178 | B2 | 6/2020 | Adams et al. |
| 10,695,531 | B2 | 6/2020 | Suzuki |
| 10,702,293 | B2 | 7/2020 | Adams et al. |
| 10,709,462 | B2 | 7/2020 | Nguyen et al. |
| 10,709,872 | B2 | 7/2020 | Alvarez et al. |
| 10,758,255 | B2 | 9/2020 | Adams |
| 10,797,684 | B1 | 10/2020 | Benz et al. |
| 10,799,688 | B2 | 10/2020 | Calhoun |
| 10,842,567 | B2 | 11/2020 | Grace et al. |
| 10,850,075 | B2 | 12/2020 | Tarunaga |
| 10,857,329 | B2 | 12/2020 | Davies |
| 10,933,225 | B2 | 3/2021 | Campbell |
| 10,952,740 | B2 | 3/2021 | Dasnurkar et al. |
| 10,952,790 | B2 | 3/2021 | Haverkost et al. |
| 10,959,743 | B2 | 3/2021 | Adams et al. |
| 10,966,737 | B2 | 4/2021 | Nguyen |
| 10,967,156 | B2 | 4/2021 | Gulachenski |
| 10,973,538 | B2 | 4/2021 | Hakala et al. |
| 10,974,028 | B2 | 4/2021 | Buller et al. |
| 10,980,987 | B2 | 4/2021 | Tarunaga |
| 11,000,299 | B2 | 5/2021 | Hawkins et al. |
| 11,020,135 | B1 | 6/2021 | Hawkins |
| 11,026,707 | B2 | 6/2021 | Ku et al. |
| 11,040,176 | B2 | 6/2021 | Blanchard et al. |
| 11,058,492 | B2 | 7/2021 | Grace et al. |
| 11,076,874 | B2 | 8/2021 | Hakala et al. |
| 11,116,939 | B2 | 9/2021 | Jamous et al. |
| 11,141,131 | B2 | 10/2021 | Stigall |
| 11,179,169 | B2 | 11/2021 | Brouillete et al. |
| 11,207,493 | B2 | 12/2021 | Suzuki et al. |
| 11,213,661 | B2 | 1/2022 | Spindler |
| 11,229,772 | B2 | 1/2022 | Nita |
| 11,229,776 | B2 | 1/2022 | Kugler et al. |
| 11,246,659 | B2 | 2/2022 | Grace et al. |
| 11,253,681 | B2 | 2/2022 | Williams |
| 11,266,817 | B2 | 3/2022 | Cope et al. |
| 11,389,171 | B2 | 7/2022 | Goldsmith |
| 11,389,628 | B2 | 7/2022 | Spencer |
| 11,395,669 | B2 | 7/2022 | O'Malley et al. |
| 11,399,862 | B2 | 8/2022 | Massimini et al. |
| 11,406,452 | B2 | 8/2022 | Efremkin |
| 11,406,799 | B2 | 8/2022 | McEvaddy et al. |
| 11,484,327 | B2 | 11/2022 | Anderson et al. |
| 11,540,848 | B2 | 1/2023 | Cai et al. |
| 11,564,729 | B2 | 1/2023 | Walzman |
| 11,602,363 | B2 | 3/2023 | Nguyen |
| 11,633,200 | B2 | 4/2023 | Anderson et al. |
| 11,672,585 | B2 | 6/2023 | Schultheis |
| 11,672,599 | B2 | 6/2023 | Schultheis et al. |

(56) References Cited

U.S. PATENT DOCUMENTS 11,707,323 B2 7/2023 Schultheis et al.
11,771,449 B2 10/2023 Adams et al.
11,779,363 B2 10/2023 Vo
11,826,530 B2 11/2023 Suzuki
11,839,391 B2 12/2023 Schultheis et al.
11,911,054 B2 2/2024 Singla
11,911,056 B2 2/2024 Anderson et al.
11,918,285 B2 3/2024 Sun et al.
11,944,331 B2 4/2024 Anderson et al.
11,950,793 B2 4/2024 Nguyen
12,011,185 B2 6/2024 Vo
12,023,098 B2 7/2024 Nguyen
12,035,932 B1 7/2024 Nunes
12,076,077 B2 9/2024 Mori
12,144,516 B2 11/2024 Betelia
12,178,458 B1 12/2024 Betelia et al.
12,193,691 B2 1/2025 Adams
2001/0016761 A1 8/2001 Rudie
2001/0018569 A1 8/2001 Erbel
2001/0020164 A1 9/2001 Papademetriou
2001/0049464 A1 12/2001 Ganz
2001/0051784 A1 12/2001 Brisken
2002/0045811 A1 4/2002 Kittrell et al.
2002/0052621 A1 5/2002 Fried et al.
2002/0065512 A1 5/2002 Fjield et al.
2002/0082553 A1 6/2002 Duchamp
2002/0183620 A1 12/2002 Tearney
2002/0183729 A1 12/2002 Farr et al.
2002/0188204 A1 12/2002 McNamara et al.
2003/0009157 A1 1/2003 Levine et al.
2003/0050632 A1 3/2003 Fjield et al.
2003/0065316 A1 4/2003 Levine et al.
2003/0114901 A1 6/2003 Loeb et al.
2003/0125719 A1 7/2003 Furnish
2003/0144654 A1 7/2003 Hilal
2003/0176873 A1 9/2003 Chernenko et al.
2004/0002677 A1 1/2004 Gentsler
2004/0024349 A1 2/2004 Flock et al.
2004/0073251 A1 4/2004 Weber
2004/0097996 A1 5/2004 Rabiner
2004/0133254 A1 7/2004 Sterzer et al.
2004/0162508 A1 8/2004 Uebelacker
2004/0210278 A1 10/2004 Boll
2004/0243119 A1 12/2004 Lane et al.
2004/0249401 A1 12/2004 Rabiner
2004/0254570 A1 12/2004 Hadsjicostis
2005/0010095 A1 1/2005 Stewart et al.
2005/0021013 A1 1/2005 Visuri
2005/0080396 A1 4/2005 Rontal
2005/0113722 A1 5/2005 Schultheiss
2005/0171437 A1 8/2005 Carberry
2005/0171527 A1 8/2005 Bhola
2005/0251131 A1 11/2005 Lesh
2005/0259319 A1 11/2005 Brooker
2005/0273014 A1 12/2005 Gianchandani et al.
2005/0277839 A1 12/2005 Alderman et al.
2006/0033241 A1 2/2006 Schewe et al.
2006/0084966 A1 4/2006 Maguire et al.
2006/0098921 A1 5/2006 Benaron et al.
2006/0142703 A1 6/2006 Carter
2006/0190022 A1 8/2006 Beyar et al.
2006/0200039 A1 9/2006 Brockway et al.
2006/0221528 A1 10/2006 Li et al.
2006/0241524 A1 10/2006 Lee et al.
2006/0241572 A1 10/2006 Zhou
2006/0241733 A1 10/2006 Zhang et al.
2006/0270976 A1 11/2006 Savage et al.
2007/0027524 A1 2/2007 Johnson
2007/0043340 A1 2/2007 Thyzel
2007/0060990 A1 3/2007 Satake
2007/0088380 A1 4/2007 Hirszowicz et al.
2007/0118057 A1 5/2007 Ein-gal
2007/0142779 A1 6/2007 Duane
2007/0142819 A1 6/2007 El-Nounou et al.
2007/0142821 A1 6/2007 Hennessy et al.
2007/0142856 A1 6/2007 Jang
2007/0179496 A1 8/2007 Swoyer
2007/0239082 A1 10/2007 Schultheiss et al.
2007/0255270 A1 11/2007 Carney
2007/0264353 A1 11/2007 Myntti et al.
2007/0270897 A1 11/2007 Skerven
2007/0280311 A1 12/2007 Hofmann
2007/0299392 A1 12/2007 Beyar et al.
2008/0033519 A1 2/2008 Burwell
2008/0081950 A1 4/2008 Koenig et al.
2008/0086118 A1 4/2008 Lai
2008/0095714 A1 4/2008 Castella et al.
2008/0097251 A1 4/2008 Babaev
2008/0108867 A1 5/2008 Zhou
2008/0114341 A1 5/2008 Thyzel
2008/0132810 A1 6/2008 Scoseria et al.
2008/0175539 A1 7/2008 Brown
2008/0195088 A1 8/2008 Farr et al.
2008/0214891 A1 9/2008 Slenker et al.
2008/0221550 A1 9/2008 Lee
2008/0281157 A1 11/2008 Miyagi et al.
2008/0296152 A1 12/2008 Voss
2008/0319356 A1 12/2008 Cain et al.
2009/0036803 A1 2/2009 Warlick et al.
2009/0043300 A1 2/2009 Reitmajer et al.
2009/0054881 A1 2/2009 Krespi
2009/0097806 A1 4/2009 Viellerobe et al.
2009/0118741 A1 5/2009 Lebet
2009/0125007 A1 5/2009 Splinter
2009/0131921 A1 5/2009 Kurtz et al.
2009/0157066 A1 6/2009 Satake
2009/0192495 A1 7/2009 Ostrovsky et al.
2009/0240242 A1 9/2009 Neuberger
2009/0247945 A1 10/2009 Levit
2009/0281531 A1 11/2009 Rizoiu
2009/0292296 A1 11/2009 Pansky
2009/0296751 A1 12/2009 Kewitsch et al.
2009/0299327 A1 12/2009 Tilson et al.
2009/0306533 A1 12/2009 Rousche
2009/0312768 A1 12/2009 Hawkins et al.
2010/0016862 A1 1/2010 Hawkins et al.
2010/0036238 A1 2/2010 Neidert
2010/0036294 A1 2/2010 Mantell et al.
2010/0063491 A1 3/2010 Verhagen
2010/0094209 A1 4/2010 Drasler et al.
2010/0114020 A1 5/2010 Hawkins et al.
2010/0114065 A1 5/2010 Hawkins et al.
2010/0125268 A1 5/2010 Gustus et al.
2010/0160838 A1 6/2010 Krespi
2010/0160903 A1 6/2010 Krespi
2010/0168572 A1 7/2010 Sliwa
2010/0168836 A1 7/2010 Kassab
2010/0168862 A1 7/2010 Edie et al.
2010/0179632 A1 7/2010 Bruszewski et al.
2010/0191089 A1 7/2010 Stebler et al.
2010/0198114 A1 8/2010 Novak et al.
2010/0199773 A1 8/2010 Zhou
2010/0222786 A1 9/2010 Kassab
2010/0234875 A1 9/2010 Allex et al.
2010/0256535 A1 10/2010 Novak et al.
2010/0265733 A1 10/2010 O'Leary
2010/0286791 A1 11/2010 Goldsmith
2010/0316333 A1 12/2010 Luther
2011/0028868 A1 2/2011 Spector
2011/0034832 A1 2/2011 Cioanta et al.
2011/0059415 A1 3/2011 Kasenbacher
2011/0082452 A1 4/2011 Melsky
2011/0082534 A1 4/2011 Wallace
2011/0118634 A1 5/2011 Golan
2011/0144502 A1 6/2011 Zhou et al.
2011/0184244 A1 7/2011 Kagaya et al.
2011/0208185 A1 8/2011 Diamant et al.
2011/0213349 A1 9/2011 Brown
2011/0245740 A1 10/2011 Novak et al.
2011/0257641 A1 10/2011 Hastings et al.
2011/0263921 A1 10/2011 Vrba et al.
2011/0275990 A1 11/2011 Besser et al.
2011/0306956 A1 12/2011 Islam
2012/0064141 A1 3/2012 Andreacchi et al.

(56) References Cited

U.S. PATENT DOCUMENTS

2012/0071715 A1 3/2012 Beyar et al.
2012/0071867 A1 3/2012 Ryan
2012/0071889 A1 3/2012 Mantell et al.
2012/0089132 A1 4/2012 Dick et al.
2012/0095335 A1 4/2012 Sverdlik et al.
2012/0095461 A1 4/2012 Herscher et al.
2012/0116289 A1 5/2012 Hawkins et al.
2012/0116486 A1 5/2012 Naga et al.
2012/0123331 A1 5/2012 Satake
2012/0123399 A1 5/2012 Belikov
2012/0143131 A1 6/2012 Tun
2012/0157892 A1 6/2012 Reitmajer et al.
2012/0203255 A1 8/2012 Hawkins et al.
2012/0221013 A1 8/2012 Hawkins et al.
2012/0232409 A1 9/2012 Stahmann
2012/0296367 A1 11/2012 Grovender et al.
2012/0323211 A1 12/2012 Ogle
2012/0330293 A1 12/2012 Arai
2013/0030431 A1 1/2013 Adams
2013/0030447 A1 1/2013 Adams
2013/0041355 A1 2/2013 Heeren et al.
2013/0046207 A1 2/2013 Capelli
2013/0046293 A1 2/2013 Arai et al.
2013/0053762 A1 2/2013 Rontal et al.
2013/0060234 A1 3/2013 Besser
2013/0110003 A1 5/2013 Surti
2013/0116714 A1 5/2013 Adams et al.
2013/0165764 A1 6/2013 Scheuermann
2013/0190803 A1 7/2013 Angel et al.
2013/0197614 A1 8/2013 Gustus
2013/0218054 A1 8/2013 Sverdlik et al.
2013/0226131 A1 8/2013 Bacino et al.
2013/0253466 A1 9/2013 Campbell
2013/0274726 A1 10/2013 Takayama
2013/0345617 A1 12/2013 Wallace
2014/0005576 A1 1/2014 Adams
2014/0005706 A1 1/2014 Gelfand et al.
2014/0012186 A1 1/2014 Thyzel
2014/0039002 A1 2/2014 Diodone et al.
2014/0039358 A1 2/2014 Zhou et al.
2014/0039513 A1 2/2014 Hakala
2014/0046229 A1 2/2014 Hawkins et al.
2014/0046353 A1 2/2014 Adams
2014/0052146 A1 2/2014 Curtis et al.
2014/0052147 A1 2/2014 Hakala et al.
2014/0058294 A1 2/2014 Gross et al.
2014/0074111 A1 3/2014 Hakala
2014/0128848 A1 5/2014 Appling et al.
2014/0153087 A1 6/2014 Hutchings et al.
2014/0155990 A1 6/2014 Nyuli
2014/0180069 A1 6/2014 Millett
2014/0180126 A1 6/2014 Millett
2014/0180134 A1 6/2014 Hoseit
2014/0188094 A1 7/2014 Islam
2014/0228829 A1 8/2014 Schmitt
2014/0257144 A1 9/2014 Capelli et al.
2014/0257148 A1 9/2014 Jie
2014/0276573 A1 9/2014 Miesel
2014/0288570 A1 9/2014 Adams
2014/0309536 A1 10/2014 Douk et al.
2014/0336626 A1 11/2014 Jiang
2014/0336637 A1 11/2014 Agrawal
2014/0357997 A1 12/2014 Hartmann
2015/0003900 A1 1/2015 Ullrich et al.
2015/0005576 A1 1/2015 Diodone et al.
2015/0039002 A1 2/2015 Hawkins
2015/0057648 A1 2/2015 Swift et al.
2015/0071591 A1 3/2015 Chen
2015/0073430 A1 3/2015 Hakala et al.
2015/0080875 A1 3/2015 Kasprzyk et al.
2015/0100048 A1 4/2015 Hiereth et al.
2015/0105715 A1 4/2015 Pikus et al.
2015/0119870 A1 4/2015 Rudie
2015/0126990 A1 5/2015 Sharma
2015/0141764 A1 5/2015 Harks et al.
2015/0250542 A1 9/2015 Islam
2015/0276689 A1 10/2015 Watanabe et al.
2015/0313732 A1 11/2015 Fulton, III
2015/0320432 A1 11/2015 Adams
2015/0342678 A1 12/2015 Deladurantaye et al.
2015/0342681 A1 12/2015 Lee
2015/0359432 A1 12/2015 Ehrenreich
2015/0359557 A1 12/2015 Shimokawa
2016/0008016 A1 1/2016 Cioanta et al.
2016/0016016 A1 1/2016 Taylor et al.
2016/0018602 A1 1/2016 Govari et al.
2016/0022294 A1 1/2016 Cioanta et al.
2016/0038087 A1 2/2016 Hunter
2016/0095610 A1 4/2016 Lipowski et al.
2016/0135828 A1 5/2016 Hawkins et al.
2016/0135891 A1 5/2016 Feldman
2016/0143522 A1 5/2016 Ransbury
2016/0151639 A1 6/2016 Scharf et al.
2016/0183819 A1 6/2016 Burnett
2016/0183957 A1 6/2016 Hakala et al.
2016/0184020 A1 6/2016 Kowalewski et al.
2016/0184022 A1 6/2016 Grace et al.
2016/0184023 A1 6/2016 Grace et al.
2016/0184526 A1 6/2016 Beyar
2016/0184570 A1 6/2016 Grace et al.
2016/0228187 A1 8/2016 Gross
2016/0234534 A1 8/2016 Kitahara et al.
2016/0262784 A1 9/2016 Grace et al.
2016/0270806 A1 9/2016 Wallace
2016/0287278 A1 10/2016 Stigall et al.
2016/0302762 A1 10/2016 Stigall et al.
2016/0324564 A1 11/2016 Gerlach et al.
2016/0331389 A1 11/2016 Hakala et al.
2016/0339204 A1 11/2016 Williams
2016/0367274 A1 12/2016 Wallace
2016/0367275 A1 12/2016 Wallace
2017/0049463 A1 2/2017 Popovic et al.
2017/0056035 A1 3/2017 Adams
2017/0086867 A1 3/2017 Adams
2017/0119469 A1 5/2017 Shimizu et al.
2017/0119470 A1 5/2017 Diamant et al.
2017/0135709 A1 5/2017 Nguyen et al.
2017/0151421 A1 6/2017 Asher
2017/0192242 A1 7/2017 Laycock
2017/0209050 A1 7/2017 Fengler et al.
2017/0265942 A1 9/2017 Grace et al.
2017/0303946 A1 10/2017 Ku et al.
2017/0311965 A1 11/2017 Adams
2017/0333105 A1* 11/2017 Newell .................. A61B 90/98
2018/0008348 A1 1/2018 Grace et al.
2018/0042661 A1 2/2018 Long
2018/0042677 A1 2/2018 Yu et al.
2018/0045897 A1 2/2018 Chia
2018/0049877 A1 2/2018 Venkatasubramanian
2018/0085174 A1 3/2018 Radtke et al.
2018/0092763 A1 4/2018 Dagan et al.
2018/0095287 A1 4/2018 Jeng et al.
2018/0098779 A1 4/2018 Betelia et al.
2018/0147606 A1 5/2018 Brouillette et al.
2018/0152568 A1 5/2018 Thumpudi et al.
2018/0169392 A1 6/2018 Franklin
2018/0206867 A1 7/2018 Allen
2018/0214677 A1 8/2018 Tarunaga
2018/0238675 A1 8/2018 Wan
2018/0256250 A1 9/2018 Adams et al.
2018/0280005 A1 10/2018 Parmentier
2018/0303501 A1 10/2018 Hawkins
2018/0303503 A1 10/2018 Eggert et al.
2018/0303504 A1 10/2018 Eggert et al.
2018/0304053 A1 10/2018 Eggert et al.
2018/0323571 A1 11/2018 Brown et al.
2018/0333043 A1 11/2018 Teriluc
2018/0360482 A1 12/2018 Nguyen
2019/0029702 A1 1/2019 De Cicco
2019/0029703 A1 1/2019 Wasdyke et al.
2019/0069916 A1 3/2019 Hawkins et al.
2019/0072378 A1 3/2019 Hane et al.
2019/0097380 A1 3/2019 Luft et al.
2019/0099588 A1 4/2019 Ramanath et al.

(56) References Cited

U.S. PATENT DOCUMENTS

| | | | |
|---|---|---|---|
| 2019/0104933 | A1 | 4/2019 | Stern |
| 2019/0117242 | A1 | 4/2019 | Lawinger |
| 2019/0150960 | A1 | 5/2019 | Nguyen et al. |
| 2019/0150961 | A1 | 5/2019 | Tozzi |
| 2019/0159792 | A1 | 5/2019 | Panian |
| 2019/0167349 | A1 | 6/2019 | Shamay |
| 2019/0175111 | A1 | 6/2019 | Genereux et al. |
| 2019/0175300 | A1 | 6/2019 | Horn |
| 2019/0175372 | A1 | 6/2019 | Boyden et al. |
| 2019/0175407 | A1 | 6/2019 | Bacher |
| 2019/0209368 | A1 | 7/2019 | Park et al. |
| 2019/0232066 | A1 | 8/2019 | Lim et al. |
| 2019/0247680 | A1 | 8/2019 | Mayer |
| 2019/0262594 | A1 | 8/2019 | Ogata et al. |
| 2019/0265419 | A1 | 8/2019 | Tayebati |
| 2019/0282249 | A1 | 9/2019 | Tran et al. |
| 2019/0282250 | A1 | 9/2019 | Tran et al. |
| 2019/0285803 | A1 | 9/2019 | Van Zuylen |
| 2019/0321100 | A1 | 10/2019 | Masotti et al. |
| 2019/0321101 | A1 | 10/2019 | Massoti et al. |
| 2019/0328259 | A1 | 10/2019 | Deno et al. |
| 2019/0365400 | A1 | 12/2019 | Adams et al. |
| 2019/0380589 | A1 | 12/2019 | Lloret |
| 2019/0388002 | A1 | 12/2019 | Bozsak et al. |
| 2019/0388110 | A1 | 12/2019 | Nguyen et al. |
| 2019/0388133 | A1 | 12/2019 | Sharma |
| 2019/0388151 | A1 | 12/2019 | Bhawalkar |
| 2019/0388654 | A1 | 12/2019 | Chou |
| 2020/0000484 | A1 | 1/2020 | Hawkins |
| 2020/0008856 | A1 | 1/2020 | Harmouche |
| 2020/0022754 | A1 | 1/2020 | Cottone |
| 2020/0038087 | A1 | 2/2020 | Harmouche |
| 2020/0046429 | A1 | 2/2020 | Tschida et al. |
| 2020/0046949 | A1 | 2/2020 | Chisena et al. |
| 2020/0054352 | A1 | 2/2020 | Brouillette et al. |
| 2020/0060814 | A1 | 2/2020 | Murphy |
| 2020/0061931 | A1 | 2/2020 | Brown et al. |
| 2020/0069371 | A1 | 3/2020 | Brown et al. |
| 2020/0085458 | A1 | 3/2020 | Nguyen et al. |
| 2020/0085459 | A1 | 3/2020 | Adams |
| 2020/0101269 | A1 | 4/2020 | Hayes |
| 2020/0107960 | A1 | 4/2020 | Bacher |
| 2020/0108236 | A1 | 4/2020 | Salazar et al. |
| 2020/0129195 | A1 | 4/2020 | McGowan et al. |
| 2020/0129741 | A1 | 4/2020 | Kawwas |
| 2020/0155812 | A1 | 5/2020 | Zhang et al. |
| 2020/0197019 | A1 | 6/2020 | Harper |
| 2020/0205890 | A1 | 7/2020 | Harlev |
| 2020/0214726 | A1 | 7/2020 | Anand et al. |
| 2020/0246032 | A1 | 8/2020 | Betelia et al. |
| 2020/0289202 | A1 | 9/2020 | Miyagawa et al. |
| 2020/0297366 | A1 | 9/2020 | Nguyen et al. |
| 2020/0337717 | A1 | 10/2020 | Walzman |
| 2020/0345380 | A1 | 11/2020 | Boyle et al. |
| 2020/0383724 | A1 | 12/2020 | Adams et al. |
| 2020/0397230 | A1 | 12/2020 | Massimini et al. |
| 2020/0397453 | A1 | 12/2020 | McGowan |
| 2020/0398033 | A1 | 12/2020 | McGowan et al. |
| 2020/0405333 | A1 | 12/2020 | Massimini et al. |
| 2020/0405391 | A1 | 12/2020 | Massimini et al. |
| 2020/0406009 | A1 | 12/2020 | Massimini |
| 2020/0406010 | A1 | 12/2020 | Massimini et al. |
| 2021/0038237 | A1 | 2/2021 | Adams |
| 2021/0085347 | A1 | 3/2021 | Phan et al. |
| 2021/0085348 | A1 | 3/2021 | Nguyen |
| 2021/0085383 | A1 | 3/2021 | Vo et al. |
| 2021/0116302 | A1 | 4/2021 | Jean-Ruel |
| 2021/0128241 | A1 | 5/2021 | Schultheis |
| 2021/0137598 | A1 | 5/2021 | Cook et al. |
| 2021/0153939 | A1 | 5/2021 | Cook |
| 2021/0177442 | A1 | 6/2021 | Girdhar et al. |
| 2021/0177445 | A1 | 6/2021 | Nguyen |
| 2021/0186613 | A1 | 6/2021 | Cook |
| 2021/0212765 | A1 | 7/2021 | Verhagen |
| 2021/0220052 | A1 | 7/2021 | Cook |
| 2021/0220053 | A1 | 7/2021 | Cook |
| 2021/0244473 | A1 | 8/2021 | Cook et al. |
| 2021/0267685 | A1 | 9/2021 | Schultheis |
| 2021/0275247 | A1 | 9/2021 | Schultheis |
| 2021/0275249 | A1 | 9/2021 | Massimini et al. |
| 2021/0282792 | A1 | 9/2021 | Adams et al. |
| 2021/0290259 | A1 | 9/2021 | Hakala et al. |
| 2021/0290286 | A1 | 9/2021 | Cook |
| 2021/0290305 | A1 | 9/2021 | Cook |
| 2021/0298603 | A1 | 9/2021 | Feldman |
| 2021/0338258 | A1 | 11/2021 | Hawkins et al. |
| 2021/0353359 | A1 | 11/2021 | Cook |
| 2021/0369348 | A1 | 12/2021 | Cook |
| 2021/0378743 | A1 | 12/2021 | Massimini et al. |
| 2021/0378744 | A1 | 12/2021 | Fanier et al. |
| 2021/0386479 | A1 | 12/2021 | Massimini et al. |
| 2022/0000505 | A1 | 1/2022 | Hauser |
| 2022/0000506 | A1 | 1/2022 | Hauser |
| 2022/0000507 | A1 | 1/2022 | Hauser |
| 2022/0000508 | A1 | 1/2022 | Schmitt et al. |
| 2022/0000509 | A1 | 1/2022 | Laser et al. |
| 2022/0000551 | A1 | 1/2022 | Govari et al. |
| 2022/0001138 | A1 | 1/2022 | Howell |
| 2022/0008130 | A1 | 1/2022 | Massimini et al. |
| 2022/0008693 | A1 | 1/2022 | Humbert et al. |
| 2022/0015785 | A1 | 1/2022 | Hakala et al. |
| 2022/0021190 | A1 | 1/2022 | Pecquois |
| 2022/0022902 | A1 | 1/2022 | Spano |
| 2022/0022912 | A1 | 1/2022 | Efremkin |
| 2022/0023528 | A1 | 1/2022 | Long et al. |
| 2022/0040454 | A1 | 2/2022 | Hamm |
| 2022/0054194 | A1 | 2/2022 | Bacher et al. |
| 2022/0071704 | A1 | 3/2022 | Le |
| 2022/0168594 | A1 | 6/2022 | Mayer |
| 2022/0183738 | A1 | 6/2022 | Flores et al. |
| 2022/0218402 | A1 | 7/2022 | Schultheis |
| 2022/0249165 | A1 | 8/2022 | Cook |
| 2022/0249166 | A1 | 8/2022 | Cook et al. |
| 2022/0273324 | A1 | 9/2022 | Schultheis |
| 2022/0287732 | A1 | 9/2022 | Anderson et al. |
| 2022/0313293 | A1 | 10/2022 | Singh |
| 2022/0313359 | A1 | 10/2022 | Schultheis et al. |
| 2022/0338890 | A1 | 10/2022 | Anderson et al. |
| 2022/0354578 | A1 | 11/2022 | Cook |
| 2022/0387106 | A1 | 12/2022 | Cook |
| 2023/0013920 | A1 | 1/2023 | Massimini |
| 2023/0059327 | A1 | 2/2023 | Irisawa |
| 2023/0064371 | A1 | 3/2023 | Cook et al. |
| 2023/0137107 | A1 | 5/2023 | Cook et al. |
| 2023/0157754 | A1 | 5/2023 | Bacher et al. |
| 2023/0200906 | A1 | 6/2023 | Cook et al. |
| 2023/0233256 | A1 | 7/2023 | Cook et al. |
| 2023/0240748 | A1 | 8/2023 | Cook et al. |
| 2023/0248376 | A1 | 8/2023 | Anderson et al. |
| 2023/0255635 | A1 | 8/2023 | Schultheis et al. |
| 2023/0255688 | A1 | 8/2023 | Schultheis et al. |
| 2023/0255689 | A1 | 8/2023 | Schultheis et al. |
| 2023/0310054 | A1 | 10/2023 | Schultheis |
| 2023/0310067 | A1 | 10/2023 | Schultheis et al. |
| 2023/0310073 | A1 | 10/2023 | Adams et al. |
| 2023/0320576 | A1 | 10/2023 | Feldman |
| 2023/0338088 | A1 | 10/2023 | Massimini et al. |
| 2023/0338089 | A1 | 10/2023 | Schultheis |
| 2023/0414234 | A1 | 12/2023 | Anderson et al. |
| 2024/0001076 | A1 | 1/2024 | Gelsinger |
| 2024/0016508 | A1 | 1/2024 | Kocur |
| 2024/0016544 | A1 | 1/2024 | Schultheis et al. |
| 2024/0016545 | A1 | 1/2024 | Schultheis et al. |
| 2024/0023813 | A1 | 1/2024 | Milner |
| 2024/0032995 | A1 | 2/2024 | Schultheis et al. |
| 2024/0033002 | A1 | 2/2024 | Cook |
| 2024/0041520 | A1 | 2/2024 | Schultheis et al. |
| 2024/0050170 | A1 | 2/2024 | Fournier |
| 2024/0050696 | A1 | 2/2024 | Japuntich |
| 2024/0058060 | A1 | 2/2024 | Cook |
| 2024/0065711 | A1 | 2/2024 | Hendrickson |
| 2024/0065712 | A1 | 2/2024 | Schultheis |
| 2024/0099773 | A1 | 3/2024 | Schabert |
| 2024/0122648 | A1 | 4/2024 | Cook |

(56) References Cited

U.S. PATENT DOCUMENTS

| | | | |
|---|---|---|---|
| 2024/0165658 | A1 | 5/2024 | Fu |
| 2024/0173044 | A1 | 5/2024 | Chen et al. |
| 2024/0173526 | A1 | 5/2024 | Kofidis |
| 2024/0189543 | A1 | 6/2024 | Salinas |
| 2024/0216062 | A1 | 7/2024 | Cook |
| 2024/0260981 | A1 | 8/2024 | Betelia |
| 2024/0260982 | A1 | 8/2024 | Peterson |
| 2024/0277410 | A1 | 8/2024 | Cook |
| 2024/0277974 | A1 | 8/2024 | Oehler |
| 2024/0277980 | A1 | 8/2024 | O'Neill |
| 2024/0285296 | A1 | 8/2024 | Vo |
| 2024/0285922 | A1 | 8/2024 | Chu |
| 2024/0299051 | A1 | 9/2024 | Sidhu et al. |
| 2024/0307119 | A1 | 9/2024 | Nguyen |
| 2024/0325045 | A1 | 10/2024 | Otake |
| 2024/0382258 | A1 | 11/2024 | Schultheis |
| 2025/0025237 | A1 | 1/2025 | Cook |
| 2025/0040947 | A1 | 2/2025 | Schultheis |

FOREIGN PATENT DOCUMENTS

| | | | |
|---|---|---|---|
| CA | 2229806 | A1 | 3/1997 |
| CA | 2281519 | | 8/1998 |
| CA | 2983655 | A1 | 10/2016 |
| CA | 3209797 | | 9/2022 |
| CN | 102057422 | A | 5/2011 |
| CN | 107411805 | A | 12/2017 |
| CN | 109223100 | A | 1/2019 |
| CN | 110638501 | | 1/2020 |
| CN | 106794043 | B | 3/2020 |
| CN | 107899126 | B | 1/2022 |
| CN | 109475378 | B | 1/2022 |
| CN | 113876388 | A | 1/2022 |
| CN | 113877044 | A | 1/2022 |
| CN | 113907838 | A | 1/2022 |
| CN | 113951972 | A | 1/2022 |
| CN | 113951973 | A | 1/2022 |
| CN | 113974765 | A | 1/2022 |
| CN | 113974826 | A | 1/2022 |
| CN | 215384399 | U | 1/2022 |
| CN | 215386905 | U | 1/2022 |
| CN | 215458400 | U | 1/2022 |
| CN | 215458401 | U | 1/2022 |
| CN | 215505065 | U | 1/2022 |
| CN | 215534803 | U | 1/2022 |
| CN | 215537694 | U | 1/2022 |
| CN | 215584286 | U | 1/2022 |
| CN | 215606068 | U | 1/2022 |
| CN | 215651393 | U | 1/2022 |
| CN | 215651394 | U | 1/2022 |
| CN | 215651484 | U | 1/2022 |
| CN | 215653328 | U | 1/2022 |
| CN | 114053552 | | 2/2022 |
| CN | 115175625 | | 10/2022 |
| CN | 113993463 | A | 12/2022 |
| CN | 117752412 | | 3/2024 |
| CN | 118055734 | | 5/2024 |
| DE | 3913027 | A1 | 10/1990 |
| DE | 69431758 | | 1/2003 |
| DE | 10230626 | | 1/2004 |
| DE | 202008016760 | U1 | 3/2009 |
| DE | 102007046902 | A1 | 4/2009 |
| DE | 102008034702 | A1 | 1/2010 |
| DE | 102009007129 | A1 | 8/2010 |
| DE | 202010009899 | U1 | 10/2010 |
| DE | 102013201928 | A1 | 8/2014 |
| DE | 102020117713 | A1 | 1/2022 |
| EP | 0119296 | A1 | 9/1984 |
| EP | 0558297 | A2 | 9/1993 |
| EP | 0547146 | | 7/1995 |
| EP | 1179993 | A1 | 2/2002 |
| EP | 1946712 | A1 | 7/2008 |
| EP | 1453566 | | 9/2008 |
| EP | 2157569 | A2 | 2/2010 |
| EP | 2470248 | | 7/2012 |
| EP | 2879595 | A1 | 6/2015 |
| EP | 2944264 | A1 | 11/2015 |
| EP | 3226795 | A1 | 10/2017 |
| EP | 3266487 | | 1/2018 |
| EP | 3318204 | A1 | 5/2018 |
| EP | 2879607 | | 2/2019 |
| EP | 3473195 | A1 | 4/2019 |
| EP | 2961463 | | 5/2019 |
| EP | 3240603 | | 5/2019 |
| EP | 3197381 | | 3/2020 |
| EP | 3240494 | | 3/2021 |
| EP | 3522812 | | 12/2021 |
| EP | 3076881 | B1 | 1/2022 |
| EP | 3932342 | A1 | 1/2022 |
| EP | 3936140 | A1 | 1/2022 |
| EP | 3960099 | | 3/2022 |
| EP | 4051154 | A1 | 9/2022 |
| EP | 4129213 | | 2/2023 |
| EP | 4277537 | | 11/2023 |
| EP | 4297669 | | 1/2024 |
| EP | 4146322 | | 4/2024 |
| EP | 3182931 | | 6/2024 |
| EP | 3950036 | | 8/2024 |
| EP | 4034005 | | 12/2024 |
| GB | 1082397 | A | 9/1967 |
| JP | H05264763 | | 10/1993 |
| JP | 1996089511 | | 4/1996 |
| JP | H09117407 | | 5/1997 |
| JP | 2001520070 | | 10/2001 |
| JP | 2004519296 | | 7/2004 |
| JP | 2008506447 | | 3/2008 |
| JP | 2008083273 | | 4/2008 |
| JP | 2009519777 | | 5/2009 |
| JP | 2009213589 | | 9/2009 |
| JP | 2011524203 | | 9/2011 |
| JP | 4805208 | | 11/2011 |
| JP | 4808620 | | 11/2011 |
| JP | 2012505050 | | 3/2012 |
| JP | 2014123147 | | 7/2014 |
| JP | A2014516614 | | 7/2014 |
| JP | A2015522344 | | 8/2015 |
| JP | 2015217215 | | 12/2015 |
| JP | 2018538077 | | 12/2018 |
| JP | 2024511710 | | 3/2024 |
| KR | 10-2005-0098932 | A | 10/2005 |
| KR | 10-2008-0040111 | A | 5/2008 |
| KR | 10-2016-0090877 | A | 8/2016 |
| KR | 20180054041 | | 5/2018 |
| WO | 92/03095 | A1 | 3/1992 |
| WO | WO9208515 | | 5/1992 |
| WO | WO9524867 | | 9/1995 |
| WO | 00/67648 | A1 | 11/2000 |
| WO | WO0103599 | | 1/2001 |
| WO | 2006/006169 | A2 | 1/2006 |
| WO | 2009/121017 | A1 | 10/2009 |
| WO | 2009/149321 | A1 | 12/2009 |
| WO | 2009/152352 | A2 | 12/2009 |
| WO | 2010/042653 | A1 | 4/2010 |
| WO | 2011/094379 | A1 | 8/2011 |
| WO | 2011/126580 | A2 | 10/2011 |
| WO | 2012/025833 | A2 | 3/2012 |
| WO | 2012/052924 | A1 | 4/2012 |
| WO | WO2012042619 | | 4/2012 |
| WO | WO2012058156 | | 5/2012 |
| WO | 2012/120495 | A2 | 9/2012 |
| WO | 2013/119662 | A1 | 8/2013 |
| WO | 2013/169807 | A1 | 11/2013 |
| WO | 2014/022867 | A1 | 2/2014 |
| WO | 2014/025397 | A1 | 2/2014 |
| WO | 2014/138582 | A2 | 9/2014 |
| WO | WO2014138582 | | 9/2014 |
| WO | 2015/056662 | A1 | 4/2015 |
| WO | 2015/177790 | A1 | 11/2015 |
| WO | WO2016014999 | | 1/2016 |
| WO | 2016/089683 | A1 | 6/2016 |
| WO | 2016/090175 | A1 | 6/2016 |
| WO | WO2016098670 | | 6/2016 |
| WO | 2016/109739 | A1 | 7/2016 |
| WO | WO2016143556 | | 9/2016 |

(56) References Cited

FOREIGN PATENT DOCUMENTS

| | | |
|---|---|---|
| WO | 2017/192869 A1 | 11/2017 |
| WO | 2018/022593 A1 | 2/2018 |
| WO | 2018/022641 A1 | 2/2018 |
| WO | 2018/083666 A1 | 5/2018 |
| WO | 2018/175322 A1 | 9/2018 |
| WO | WO2018175322 | 9/2018 |
| WO | 2018/191013 A1 | 10/2018 |
| WO | 2019/222843 A1 | 11/2019 |
| WO | 2020/056031 A1 | 3/2020 |
| WO | 2020/086361 A1 | 4/2020 |
| WO | 2020/157648 A1 | 8/2020 |
| WO | 2020/256693 A1 | 12/2020 |
| WO | 2020/256898 A1 | 12/2020 |
| WO | 2020/256949 A1 | 12/2020 |
| WO | 2021/061451 A1 | 4/2021 |
| WO | 2021/067563 A1 | 4/2021 |
| WO | 2021/101766 A1 | 5/2021 |
| WO | 2022/007490 A1 | 1/2022 |
| WO | 2022/008440 A1 | 1/2022 |
| WO | 2022/055784 A1 | 3/2022 |
| WO | 2022/125525 A1 | 6/2022 |
| WO | 2022/154954 A1 | 7/2022 |
| WO | 2022/173719 A1 | 8/2022 |
| WO | 2022/187058 A1 | 9/2022 |
| WO | WO2022183075 | 9/2022 |
| WO | 2022/216488 A1 | 10/2022 |
| WO | 2022/240674 A1 | 11/2022 |
| WO | 2022/260932 A1 | 12/2022 |
| WO | WO2023107334 | 6/2023 |
| WO | WO2024079108 | 4/2024 |
| WO | WO2024107418 | 5/2024 |

OTHER PUBLICATIONS

Shen, Yajie et al. "High-peak-power and narrow-linewidth Q-switched Ho: YAG laser in-band pumped at 1931 nm." Applied Physics Express 13.5 (2020): 052006. (Year 2020).

Definition of ablation—NCI Dictionary of Cancer Terms—NCI, National Cancer Institute, p. 1 (Year:2025).

Daemen, J., Tovar Forero, M.N, "The Coronary Intravascular Lithotripsy System", ICR Journal, 2019; 14(3); 174-181.

Butt, N., Khalid, N., Shlofmitz, E., "Intravascular Lithotripsy"; NCBI Bookshelf. A service of the National Library of Medicine, National Institutes of Health; StatPearls Publishing, 2023.

PathFinder Digital, "Free Space Optics vs. Fiber Optics", 2023.

Poduval, R., et al. "Optical fiber ultrasound transmitter with electrospun carbon nanotube-polymer composite", Appl. Phys. Lett., 2017, vol. 110, 223701, American Institute of Physics.

Preisack, M., et al. "Ultrafast imaging of tissue ablation by a XeCl excimer laser in saline", Lasers in Surgery and Medicine, 1992, pp. 520-527, vol. 12, Wiley-Liss Inc.

Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.

Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.

Reichel, E., et al. "Laser-induced Shock Wave Lithotripsy with a Regenerative Energy Converter", Lasers in Medical Science, 1992, pp. 423-425, vol. 7, Bailliere Tindall.

Roberts, Randy M., et al. "The Energy Partition of Underwater Sparks", The Journal of the Acoustical Society of America, 1996, pp. 3465-3475, vol. 99, No. 6, Acoustical Society of America.

Roberts, Randy M., et al. "The Energy Partition of Underwater Sparks", The Journal of the Acoustical Society of America, Jun. 1996, pp. 3465-3474, Acoustical Society of America, Austin, TX, USA.

Sacher et al., "Comparison of Manual Vs Automatic Annotation to Identify Abnormal Substrate for Scar Related VT Ablation." LIRYC Institute, Bordeaux University Hospital, France (ID 1336). Poster for conference in San Francisco, May 8-11, 2019.

Schafter+Kirchhoff, Laser Beam Couplers series 60SMS for coupling into single-mode and polarization-maintaining fiber cables, Schafter+Kirchhoff, pp. 1-5, Germany. Dec. 2, 2021.

Shangguan, H., et al. "Effects of Material Properties on Laser-induced Bubble Formation in Absorbing Liquids and on Submerged Targets", Diagnostic and Therapeutic Cardiovascular Interventions VII, SPIE, 1997, pp. 783-791, vol. 2869, SPIE.

Shangguan, HanQun et al. "Effects of Material Properties on Laser-induced Bubble Formation in Absorbing Liquids and on Submerged Targets", SPIE, 1997, pp. 783-791, vol. 2869.

Shariat, Mohammad H., et al. "Localization of the ectopic spiral electrical source using intracardiac electrograms during atrial fibrillation." 2015 IEEE 28th Canadian Conference on Electrical and Computer Engineering (CCECE). IEEE, 2015.

Shariat, Mohammad Hassan. Processing the intracardiac electrogram for atrial fibrillation ablation. Diss. Queen's University (Canada), 2016.

Shen, Y., et al. "Theoretical and experimental studies of directivity of sound field generated by pulsed laser induced breakdown in liquid water", SPIE, 2013, pp. 8796141-8796148, vol. 8796, SPIE.

Smith, A., et al. "Bulk and surface laser damage of silica by picosecond and nanosecond pulses at 1064 nm", Applied Optics, 2008, pp. 4812-4832, vol. 47, No. 26, Optical Society of America.

Smith, A., et al. "Deterministic Nanosecond Laser-Induced Breakdown Thresholds in Pure and Yb3 Doped Fused Silica", SPIE, 2007, pp. 6453171-64531712, vol. 6453, SPIE.

Smith, A., et al. "Nanosecond laser-induced breakdown in pure and Yb3 doped fused silica", SPIE, 2007, vol. 6403, SPIE.

Smith, A., et al. "Optical Damage Limits to Pulse Energy From Fibers", IEEE Journal of Selected Topics in Quantum Electronics, 2009, pp. 153-158, vol. 15, No. 1, IEEE.

Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.

Stelzle, F., et al. Tissue Discrimination by Uncorrected Autofluorescence Spectra: A Proof-of-Principle Study for Tissue-Specific Laser Surgery, Sensors, 2013, pp. 13717-13731, vol. 13, Basel, Switzerland.

Sun, X., et al. "Laser Induced Damage to Large Core Optical Fiber by High Peak Power Laser", Specialty Photonics Division, 2010.

Tagawa, Y., et al. "Structure of laser-induced shock wave in water", Japan Society for the Promotion of Science, 2016.

Tian, J., et al. "Distributed fiber-optic laser-ultrasound generation based on ghost-mode of tilted fiber Bragg gratings", Optics Express, Mar. 2013, pp. 6109-6114, vol. 21, No. 5, Optical Society of America.

Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc., The Netherlands.

Van Leeuwen, Ton G., et al. "Excimer Laser Induced Bubble: Dimensions, Theory, and Implications for Laser Angioplasty", Lasers in Surgery and Medicine 18, 1996, pp. 381-390, Wiley-Liss Inc., Utrecht, The Netherlands.

Van Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.

Varghese, B., et al. "Effects of polarization and absorption on laser induced optical breakdown threshold for skin rejuvenation", SPIE, Mar. 9, 2016, vol. 9740, SPIE, San Francisco, USA.

Varghese, B., et al. "Effects of polarization and apodization on laser induced optical breakdown threshold", Optics Express, Jul. 29, 2013, vol. 21, No. 15, Optical Society of America.

Varghese, B., et al. "Influence of absorption induced thermal initiation pathway on irradiance threshold for laser induced breakdown", Biomedical Optics Express, 2015, vol. 6, No. 4, Optical Society of America.

(56) References Cited

OTHER PUBLICATIONS

Versluis, M., et al. "How Snapping Shrimp Snap: Through Cavitating Bubbles", Science Mag, 2000, pp. 2114-2117, vol. 289, American Association for the Advancement of Science, Washington DC, USA.
Vesselov, L., et al. "Design and performance of thin cylindrical diffusers created in Ge-doped multimode optical fibers", Applied Optics, 2005, pp. 2754-2758, vol. 44, Issue 14, Optical Society of America.
Vogel, A. et al. "Energy balance of optical breakdown in water at nanosecond to femtosecond time scales", Applied Physics B 68, 1999, pp. 271-280, Springer-Verlag.
Vogel, A., et al. "Acoustic transient generation by laser-produced cavitation bubbles near solid boundaries", Journal Acoustical Society of America, 1988, pp. 719-731, vol. 84.
Vogel, A., et al. "Minimization of Cavitation Effects in Pulsed Laser Ablation Illustrated on Laser Angioplasty", Applied Physics, 1996, pp. 173-182, vol. 62, Springer-Verlag.
Vogel, A., et al. "Shock wave emission and cavitation bubble generation by picosecond and nanosecond optical breakdown in water", The Journal of the Acoustical Society of America, 1996, pp. 148-165, vol. 100, No. 1, Acoustical Society of America.
Whitesides, George M., et al. "Fluidic Optics", 2006, vol. 6329, SPIE, Cambridge, MA, USA.
Yan, D., et al. "Study of the Electrical Characteristics, Shock-Wave Pressure Characteristics, and Attenuation Law Based on Pulse Discharge in Water", Shock and Vibration, 2016, pp. 1-11, vol. 2016, Article ID 6412309, Hindawi Publishing Corporation.
Zhang, Q., et al. "Improved Instruments and Methods for the Photographic Study of Spark-Induced Cavitation Bubbles", Water, 2018, pp. 1-12, vol. 10, No. 1683.
Zheng, W., "Optical Lenses Manufactured on Fiber Ends", IEEE, 2015, Splicer Engineering, Duncan SC USA.
Zhou et al., "Photoacoustic Imaging with fiber optic technology: A review", Science Direct; 2020.
"Bubble Dynamics and Shock Waves", Springer, 2013, Springer-Verlag, Berlin Heildelberg.
"Damage threshold of fiber facets", NKT Photonics, 2012, pp. 1-4, Denmark.
AccuCoat, "Beamsplitter: Divide, combine & conquer"; 2023.
Ali, Ziad A., et al. "Intravascular lithotripsy for treatment of stent underexpansion secondary to severe coronary calcification" 2018, European Society of Cardiology.
Ali, Ziad A., et al. "Optical Coherence Tomography Characterization of Coronary Lithoplasty for Treatment of Calcified Lesions", JACC: Cardiovascular Imaging, 2017, pp. 897-906, vol. 109, No. 8, Elsevier.
Ashok, Praveen C., et al. "Raman spectroscopy bio-sensor for tissue discrimination in surgical robotics—full article", Journal of Biophotonics, 2014, pp. 103-109, vol. 7, No. 1-2.
Ashok, Praveen C., et al. "Raman spectroscopy bio-sensor for tissue discrimination in surgical robotics—proof" Journal of Biophotonics 7, 2014, No. 1-2.
Asshauer, T., et al. "Acoustic transient generation by holmium-laser-induced cavitation bubbles", Journal of Applied Physics, Nov. 1, 1994, pp. 5007-5013, vol. 76, No. 9, American Institute of Physics.
Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.
Bian, D. C., et al. "Study on Breakdown Delay Characteristics Based on High-voltage Pulse Discharge in Water with Hydrostatic Pressure", Journal of Power Technologies 97(2), 2017, pp. 89-102.
Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.
Blackmon, Richard L., et al. "Holmium: YAG Versus Thulium Fiber Laser Lithotripsy", Lasers in Surgery and Medicine, 2010, pp. 232-236, Wiley-Liss Inc.
Bonito, Valentina, "Effects of polarization, plasma and thermal initiation pathway on irradiance threshold of laser induced optical breakdown", Philips Research, 2013, The Netherlands.
Brodmann, Marianne et al. "Safety and Performance of Lithoplasty for Treatment of Calcified Peripheral Artery Lesions", JACC, 2017, vol. 70, No. 7.
Brouillette, M., "Shock Waves at Microscales", 2003, pp. 3-12, Springer-Verlag.
Calkins, Hugh. "Three dimensional mapping of atrial fibrillation: techniques and necessity." Journal of interventional cardiac electrophysiology 13.1 (2005): 53-59.
Chen, Sung-Liang, "Review of Laser-Generated Ultrasound Transmitters and their Applications to All-Optical Ultrasound Transducers and Imaging", Appl. Sci. 2017, 7, 25.
Claverie, A., et al. "Experimental characterization of plasma formation and shockwave propagation induced by high power pulsed underwater electrical discharge", Review of Scientific Instruments, 2014, American Institute of Physics.
Colchester, R., et al. "Laser-Generated ultrasound with optica fibres using functionalised carbon nanotube composite coatings", Appl. Phys. Lett., 2014, vol. 104, 173504, American Institute of Physics.
Communication Pursuant to Article 94(3) EPC, for European Patent Application No. 18185152.8, mailed Jan. 16, 2019.
Cook, Jason R., et al. "Tissue mimicking phantoms for photoacoustic and ultrasonic imaging", Biomedical Optics Express, 2011, vol. 2, No. 11, Optical Society of America.
Costanzo, F., "Underwater Explosion Phenomena and Shock Physics", Research Gate, 2011.
Davletshin, Yevgeniy R., "A Computational Analysis of Nanoparticle-Mediated Optical Breakdown", A dissertation presented to Ryerson University in Partial Fulfillment of the requirements for the degree of Doctor of Philosophy in the Program of Physics, Toronto, Ontario, CA 2017.
De Silva, K., et al. "A Calcific, Undilatable Stenosis Lithoplasty, a New Tool in the Box?", JACC: Cardiovascular Interventions, 2017, vol. 10, No. 3, Elsevier.
Debasis, P., et al. "Continuous-wave and quasi-continuous wave thulium-doped all-fiber laser: implementationon kidney stone fragmentations", Applied Optics, Aug. 10, 2016, vol. 55, No. 23, Optical Society of America.
Deckelbaum, L., "Coronary Laser Angioplasty", Lasers in Surgery and Medicine, 1994, pp. 101-110, vol. 14, Wiley-Liss Inc., Conneticuit, USA.
Deckelbaum, Lawrence I., "Coronary Laser Angioplasty", Lasers in Surgery and Medicine, 1994, pp. 101-110, Wiley-Liss Inc.
Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.
Dwyer, J. R., et al. "A study of X-ray emission from laboratory sparks in air at atmospheric pressure", Journal of Geophysical Research, 2008, vol. 113, American Geophysical Union.
Esch, E., et al. "A Simple Method for Fabricating Artificial Kidney Stones of Different Physical Properties", National Institute of Health Public Access Author Manuscript, Aug. 2010.
European Search Report, for European Patent Application No. 18185152, mailed Dec. 13, 2018.
European Search Report, for European Patent Application No. 18185152.8, mailed Dec. 20, 2018.
Forero, M., et al. "Coronary lithoplasty: a novel treatment for stent underexpansion", Cardiovascular Flashlight, 2018, European Society of Cardiology.
Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.
Hardy, L., et al. "Cavitation Bubble Dynamics during Thulium Fiber Laser Lithotripsy", SPIE BiOS, 2016, vol. 9689, SPIE.

(56) References Cited

OTHER PUBLICATIONS

Hardy, Luke A., et al. "Cavitation Bubble Dynamics During Thulium Fiber Laser Lithotripsy", SPIE, Feb. 29, 2016, vol. 9689, San Francisco, California, USA.
Hutchens, Thomas C., et al. "Detachable fiber optic tips for use in thulium fiber laser lithotripsy", Journal of Biomedical Optics, Mar. 2013, vol. 18(3), SPIE.
International Preliminary Report on Patentability dated Sep. 15, 2020 in PCT Application Serial No. PCT/US2019/022009 (related matter 30228.05.PCT).
International Search Report and Written Opinion dated Apr. 12, 2021 in PCT Application Serial No. PCT/US2020/059960 (related matter 30228.18.PCT).
International Search Report and Written Opinion dated Apr. 13, 2021 in PCT Application Serial No. PCT/US2020/064846 (related matter 30228.27.PCT).
International Search Report and Written Opinion dated Apr. 13, 2021 in PCT Application Serial No. PCT/US2021/013944 (related matter 30228.31.PCT).
International Search Report and Written Opinion dated Apr. 4, 2022 in PCT Application Serial No. PCT/US2021/062170 (related matter 30228.46.PCT).
International Search Report and Written Opinion dated Apr. 4, 2022 in PCT Application Serial No. PCT/US2021/065073 (related matter 30228.47.PCT).
International Search Report and Written Opinion dated Aug. 20, 2021 in PCT Application Serial No. PCT/US2021/031130 (related matter 30228.40.PCT).
International Search Report and Written Opinion dated Aug. 25, 2022 in PCT Application Serial No. PCTUS/2022/028035 Related matter 30228.50.PCT).
International Search Report and Written Opinion dated Jan. 20, 2020 in PCT Application Serial No. PCT/US2020/054792 (related matter 30228.20.PCT).
International Search Report and Written Opinion dated Jan. 29, 2020 in PCT Application Serial No. PCT/US2020/059961 (related matter 30228.19.PCT).
International Search Report and Written Opinion dated Jan. 3, 2020, in PCT Application Serial No. PCT/US2019/056579 (related matter 30228.07.PCT).
International Search Report and Written Opinion dated Jul. 13, 2021 in PCT Application Serial No. PCT/US2021/024216 (related matter 30228.34.PCT).
International Search Report and Written Opinion dated Jul. 20, 2018, in PCT Application Serial No. PCT/US2018/027784 (related matter 30228.03.PCT).
International Search Report and Written Opinion dated Jul. 20, 2018, in PCT Application Serial No. PCT/US2018/027801 (related to matter 30228.02.PCT).
International Search Report and Written Opinion dated Jul. 29, 2020 in PCT Application Serial No. PCT/US2020/034005 (related matter 30228.10.PCT).
International Search Report and Written Opinion dated Jun. 17, 2021 in PCT Application Serial No. PCT/US2021/020934 (related matter 30228.41.PCT).
International Search Report and Written Opinion dated Jun. 2, 2021 in PCT Application Serial No. PCT/US2021/015204 (related matter 30228.32.PCT).
International Search Report and Written Opinion dated Jun. 2, 2021 in PCT Application Serial No. PCT/US2021/018522 (related matter 30228.21.PCT).
International Search Report and Written Opinion dated Jun. 22, 2018, in Application Serial No. NL2019807, issued by the European Patent Office (related matter 30228.04.NL).
International Search Report and Written Opinion dated Jun. 22, 2021 in PCT Application Serial No. PCT/US2021/020937 (related matter 30228.24.PCT).
International Search Report and Written Opinion dated Jun. 24, 2021 in PCT Application Serial No. PCT/US2021/021272 (related matter 30228.33.PCT).
International Search Report and Written Opinion dated Jun. 27, 2018, in PCT Application Serial No. PCT/US2018/027121 (related matter 30228.01.PCT).
International Search Report and Written Opinion dated Jun. 27, 2022, in PCT Application Serial No. PCT/US2022/022460 (related matter 30228.49.PCT).
International Search Report and Written Opinion dated Jun. 28, 2022, in PCT Application Serial No. PCT/US2022/015577 (related matter 30228.43.PCT).
International Search Report and Written Opinion dated May 13, 2022 in PCT Application Serial No. PCT/US2022/017562 (related matter 30228.44.PCT).
International Search Report and Written Opinion dated May 22, 2019, in PCT Application Serial No. PCT/US2019/022009 (related matter 30228.05.PCT).
International Search Report and Written Opinion dated May 25, 2021 in PCT Application Serial No. PCT/US2021/017604 (related matter 30228.35.PCT).
International Search Report and Written Opinion dated May 29, 2019, in PCT Application Serial No. PCT/US2019/022016 (related matter 30228.06.PCT).
International Search Report and Written Opinion dated Nov. 8, 2022 in PCT Application Serial No. PCTUS/2022/039678 (Related matter 30228.52.PCT).
International Search Report and Written Opinion dated Oct. 2, 2020 in PCT Application Serial No. PCT/US2020/036107 (related matter 30228.25.PCT).
International Search Report and Written Opinion dated Sep. 11, 2020 in PCT Application Serial No. PCT/US2020/038517 (related matter 30228.13.PCT).
International Search Report and Written Opinion dated Sep. 11, 2020 in PCT Application Serial No. PCT/ US2020/038521 (related matter 30228.12.PCT).
International Search Report and Written Opinion dated Sep. 14, 2020 in PCT Application Serial No. PCT/US2020/038523 (related matter 30228.14.PCT).
International Search Report and Written Opinion dated Sep. 15, 2022 in PCT Application Serial No. PCTUS/2022/032045 Related matter 30228.51.PCT).
International Search Report and Written Opinion dated Sep. 7, 2020 in PCT Application Serial No. PCT/US2020/034642 (related matter 30228.08.PCT).
International Search Report and Written Opinion dated Sep. 9, 2020 in PCT Application Serial No. PCT/US2020/038530 (related matter 30228.15.PCT).
International Search Report and Written Opinion issued by the European Patent Office, for Serial No. PCT/US2022/053775, dated Apr. 21, 2023. (Re 45PCT).
International Search Report and Written Opinion issued by the European Patent Office, for Serial No. PCT/US2023/011497, dated Apr. 28, 2023. (Re 54PCT).
International Search Report and Written Opinion issued by the European Patent Office, for Serial No. PCT/US2023/012599, dated May 19, 2023.
International Search Report and Written Opinion, issued in Application Serial No. PCT/US2023/016152, dated Jul. 12, 2023.
International Search Report and Written Opinion, PCT Application Serial No. PCT/US2022/047691 issued Feb. 13, 2023, by the European Patent Office. (53PCT).
International Search Report and Written Opinion, PCT Application Serial No. PCT/US2022/047751 issued Feb. 10, 2023, by the European Patent Office. (56PCT).
Isner, Jeffrey M., et al. "Excimer Laser Atherectomy", Circulation, Jun. 1990, vol. 81, No. 6, American Heart Association, Dallas, TX, USA.
Israel, Douglas H., et al. "Excimer Laser-Facilitated Balloon Angioplasty of a Nondilateable Lesion", JACC, Oct. 1991, vol. 18, No. 4, American College of Cardiology, New York, USA.
Jansen, Duco E., et al. "Effect of Pulse Duration on Bubble Formation and Laser-Induced Pressure Waves During Holmium Laser Ablation", Lasers in Surgery and Medicine 18, 1996, pp. 278-293, Wiley-Liss Inc., Austin, TX, USA.

(56) References Cited

OTHER PUBLICATIONS

Jiang et al., “Multielectrode Catheter for Substrate Mapping for Scar-related VT Ablation: A Comparison Between Grid Versus Linear Configurations.” UChicago Medicine, Center for Arrhythmia Care, Chicago IL (ID 1368). Poster for conference in San Francisco, May 8-11, 2019.
Kang, H., et al. “Enhanced photocoagulation with catheter-based diffusing optical device”, Journal of Biomedical Optics, 2012, vol. 17, Issue 11, 118001, SPIE.
Kang, Hyun W., et al. “Enhanced photocoagulation with catheter based diffusing optical device”, Journal of Biomedical Optics, Nov. 2012, vol. 17(11), SPIE.
Kim, J., et al. “Optical Fiber Laser-Generated-Focused-Ultrasound Transducers for Intravascular Therapies”, IEEE, 2017.
Kostanski, Kris L., et al. “Development of Novel Tunable Light Scattering Coating Materials for Fiber Optic Diffusers in Photodynamic Cancer Therapy”, Journal of Applied Polymer Science, 2009, pp. 1516-1523, vol. 112, Wiley InterScience.
Kristiansen, M., et al. “High Voltage Water Breakdown Studies”, DoD, 1998, Alexandria, VA, USA.
Lin et al., “Photoacoustic imaging”, Science Direct; 2021.
Linz, N., et al. “Wavelength dependence of nanosecond infrared laser-induced breakdown in water: Evidence for multiphoton initiation via an intermediate state”, Physical Review, 2015, pp. 134114.1-1341141.10, vol. 91, American Physical Society.
Meng et al., “Accurate Recovery of Atrial Endocardial Potential Maps From Non-contact Electrode Data.” Auckland Bioengineering Institute. (ID 1421). May 2019.
Mirshekari, G., et al. “Shock Waves in Microchannels”, 2013, pp. 259-283, vol. 724, Cambridge University Press.
Mizeret, J. C., et al. “Cylindrical fiber optic light diffuser for medical applications”, Lasers in Surgery and Medicine, 1996, pp. 159-167, vol. 19, Issue 2, Wiley-Liss Inc., Lausanne, Switzerland.
Nademanee, Koonlawee, et al. “A new approach for catheter ablation of atrial fibrillation: mapping of the electrophysiologic substrate.” Journal of the American College of Cardiology 43.11 (2004): 2044-2053.
Nguyen, H., et al. “Fabrication of multipoint side-firing optical fiber by laser micro-ablation”, Optics Letters, May 1, 2017, vol. 42, No. 9, Optical Society of America.
Noack, J., “Influence of pulse duration on mechanical effects after laser-induced breakdown in water”, Journal of Applied Physics, 1998, pp. 7488-EOA, vol. 83, American Institute of Physics.
Noimark, Sacha, et al., “Carbon-Nanotube-PDMS Composite Coatings on Optical Fibers for All-Optical Ultrasound Imaging”, Advanced Functional Materials, 2016, pp. 8390-8396, vol. 26, Wiley-Liss Inc.
Oriel Instruments, “Introduction to Beam Splitters for Optical Research Applications”, Apr. 2014, pp. 1-9, https://www.azoptics.com/Article.aspx?ArticalD=871.
Partial Search Report and Provisional Opinion dated Feb. 19, 2021 in PCT Application Serial No. PCT/US2020/059960 (related matter 30228.18.PCT).
Partial Search Report and Provisional Opinion dated May 3, 2022 in PCT Application No. PCT/US2022/015577 (related matter 30228.43.PCT).

* cited by examiner

MANIFOLD INTEGRATED HANDLE ASSEMBLY FOR INTRAVASCULAR LITHOTRIPSY DEVICE

RELATED APPLICATION

This application claims priority on U.S. Provisional Application Ser. No. 63/309,867, filed on Feb. 14, 2022. As far as permitted, the contents of U.S. Provisional Application Ser. No. 63/309,867 are incorporated in their entirety herein by reference.

BACKGROUND

Vascular lesions within vessels in the body can be associated with an increased risk for major adverse events, such as myocardial infarction, embolism, deep vein thrombosis, stroke, and the like. Severe vascular lesions, such as severely calcified vascular lesions, can be difficult to treat and achieve patency for a physician in a clinical setting.

Vascular lesions may be treated using interventions such as drug therapy, balloon angioplasty, atherectomy, stent placement, vascular graft bypass, to name a few. Such interventions may not always be ideal or may require subsequent treatment to address the lesion.

Intravascular lithotripsy is one method that has been recently used with some success for breaking up vascular lesions within vessels in the body. Intravascular lithotripsy utilizes a combination of pressure waves and bubble dynamics that are generated intravascularly in a fluid-filled balloon catheter. In particular, during an intravascular lithotripsy treatment, a high energy source is used to generate plasma and ultimately pressure waves as well as a rapid bubble expansion within a fluid-filled balloon to crack calcification at a treatment site within the vasculature that includes one or more vascular lesions. The associated rapid bubble formation from the plasma initiation and resulting localized fluid velocity within the balloon transfers mechanical energy through the incompressible fluid to impart a fracture force on the intravascular calcium, which is opposed to the balloon wall. The rapid change in fluid momentum upon hitting the balloon wall is known as hydraulic shock, or water hammer.

There is an ongoing desire to enhance vessel patency and optimization of therapy delivery parameters within an intravascular lithotripsy catheter system in a manner that is relatively easy to control and is consistently manufacturable.

SUMMARY

The present invention is directed toward a catheter system for placement within a blood vessel having a vessel wall. The catheter system can be used by a user for treating a vascular lesion within or adjacent to the vessel wall within a body of a patient. In various embodiments, the catheter system includes a catheter shaft; a handle assembly; and a source manifold. The handle assembly is coupled to the catheter shaft. The handle assembly includes an assembly housing. The handle assembly is usable by the user to selectively position the catheter shaft near the vascular lesion. The source manifold is coupled to the assembly housing. The source manifold includes a manifold housing having a catheter shaft port that is configured to receive a portion of the catheter shaft so that the catheter shaft is coupled to the manifold housing.

In some embodiments, the source manifold is positioned substantially within the assembly housing.

In certain embodiments, the catheter system further includes a pressure sensor that is coupled to the manifold housing, the pressure sensor being configured to sense a fluid pressure of a catheter fluid within the catheter system.

In some embodiments, the handle assembly further includes circuitry that is electrically coupled to the pressure sensor.

In one embodiment, the circuitry includes a printed circuit board.

In certain embodiments, the handle assembly further includes an energy activator that is coupled to the circuitry; and the energy activator is configured to enable the user to selectively activate the catheter system.

In some embodiments, the manifold housing includes a sensor bore; and the pressure sensor is positioned within the sensor bore.

In many embodiments, the manifold housing includes a first housing member and a second housing member that are selectively attached to one another via an attachment assembly.

In some embodiments, the attachment assembly includes a first attachment member that is coupled to the first housing member and a second attachment member that is coupled to the second housing member; and the first attachment member is configured to engage the second attachment member when the first housing member is attached to the second housing member.

In one embodiment, the first attachment member includes an attachment channel; and wherein the second attachment member includes an attachment projection.

In certain embodiments, the first attachment member and the second attachment member are attached to one another with an adhesive material.

In other embodiments, the first attachment member and the second attachment member are ultrasonically sealed to one another.

In some embodiments, the catheter system further includes a balloon that is coupled to the catheter shaft, the balloon including a balloon wall that defines a balloon interior, the balloon being configured to retain a catheter fluid within the balloon interior.

In certain embodiments, the balloon is selectively inflatable with the catheter fluid to expand to an inflated state, wherein when the balloon is in the inflated state the balloon wall is configured to be positioned substantially adjacent to the vascular lesion.

In some embodiments, the catheter system further includes a pressure sensor that is coupled to the manifold housing, the pressure sensor being configured to sense a fluid pressure of the catheter fluid within the balloon interior.

In many embodiments, the catheter system further includes an energy guide that is coupled to the source manifold, the energy guide including a guide distal end that is configured to be positioned within the balloon interior.

In some embodiments, the energy guide is configured to guide energy from an energy source through the energy guide and into the balloon interior.

In certain embodiments, the energy guide guiding the energy from the energy source into the balloon interior generates a plasma bubble in the catheter fluid within the balloon interior.

In some embodiments, energy from the plasma bubble is directed toward a portion of the balloon wall that is positioned substantially adjacent to the vascular lesion.

In various embodiments, the energy guide generates one or more pressure waves in the catheter fluid that impart a force upon the vascular lesion.

In certain embodiments, the energy guide includes an optical fiber.

In some embodiments, the energy source includes a laser.

In other embodiments, the energy source is a high voltage energy source that provides pulses of high voltage.

In one embodiment, the energy guide includes an electrode pair including spaced apart electrodes that extend into the balloon interior; and pulses of high voltage from the energy source are applied to the electrodes and form an electrical arc across the electrodes.

In certain embodiments, the manifold housing includes an energy guide port; and the energy guide is coupled to the manifold housing via the energy guide port.

In some embodiments, the catheter system further includes a plurality of energy guides that are coupled to the source manifold, each of the plurality of energy guides including a guide distal end that is configured to be positioned within the balloon interior.

In many embodiments, the plurality of energy guides are coupled into the energy guide port with an optical sealing component, the optical sealing component including a seal body and a plurality of guide channels that are formed through the seal body; and each of the plurality of energy guides is configured to extend through one of the plurality of guide channels.

In certain embodiments, the manifold housing further includes a guidewire lumen port; and a guidewire lumen is coupled to the manifold housing via the guidewire lumen port.

In some embodiments, the manifold housing further includes a media inflation port; and an inflation conduit is coupled to the manifold housing via the media inflation port.

In certain embodiments, the inflation conduit is configured to guide the catheter fluid into the balloon interior.

In one embodiment, the manifold housing includes a first housing member and a second housing member that are selectively attached to one another; and each of the catheter shaft port, the energy guide port, the guidewire lumen port and the media inflation port are formed into the second housing member.

The present invention is further directed toward a method for treating a vascular lesion within or adjacent to a blood vessel within a body of a patient, including the steps of coupling a handle assembly to a catheter shaft, the handle assembly including an assembly housing; selectively positioning the catheter shaft near the vascular lesion through use of the handle assembly; and coupling a source manifold to the assembly housing, the source manifold including a manifold housing having a catheter shaft port that is configured to receive a portion of the catheter shaft so that the catheter shaft is coupled to the manifold housing.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

Figure 1:
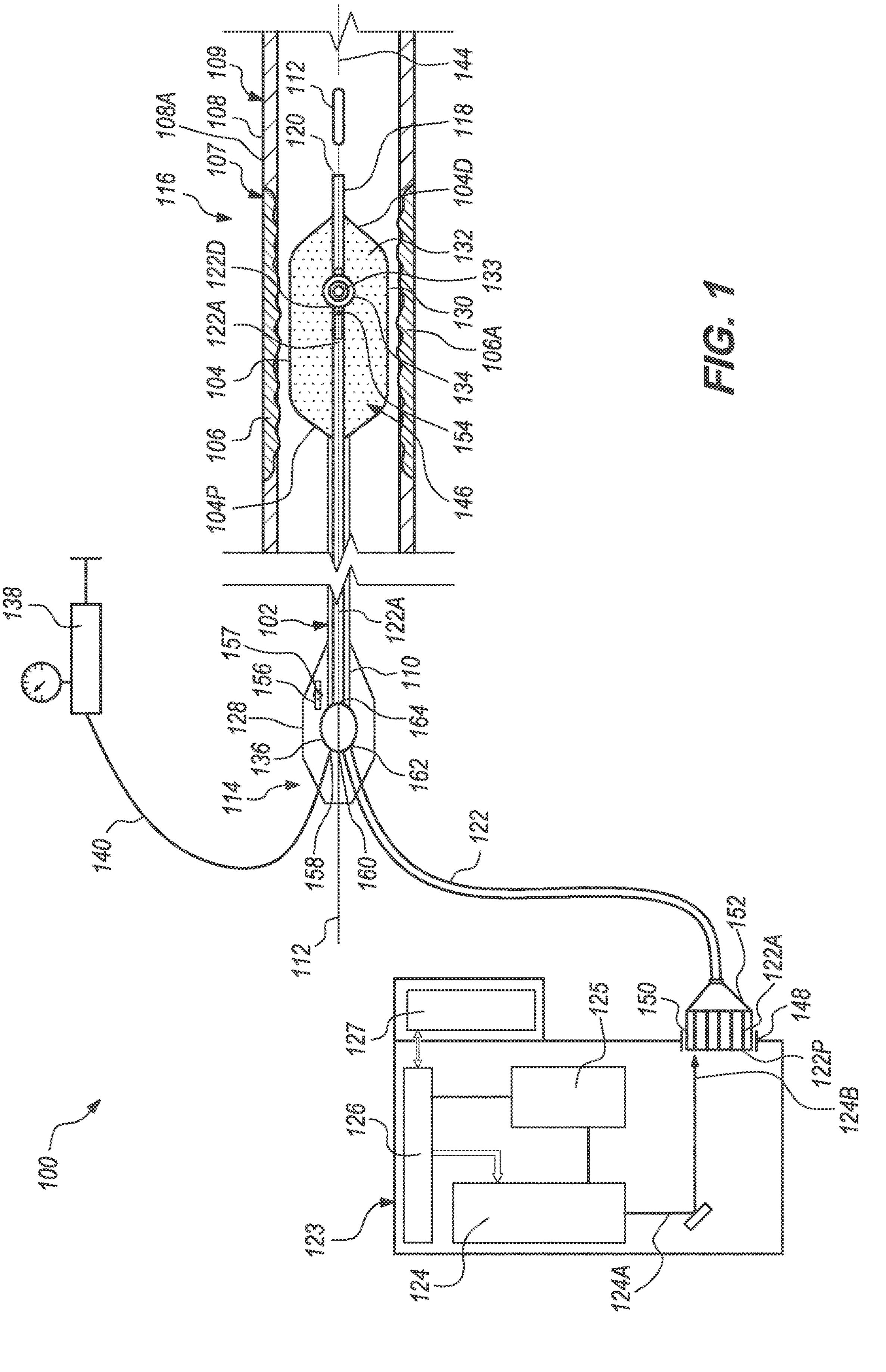
FIG. 1 is a simplified schematic cross-sectional view illustration of an embodiment of a catheter system in accordance with various embodiments, the catheter system including a handle assembly having features of the present invention, including a source manifold that is integrated into the handle assembly.

While embodiments of the present invention are susceptible to various modifications and alternative forms, specifics thereof have been shown by way of example and drawings, and are described in detail herein. It is understood, however, that the scope herein is not limited to the particular embodiments described. On the contrary, the intention is to cover modifications, equivalents, and alternatives falling within the spirit and scope herein.

DESCRIPTION

Treatment of vascular lesions can reduce major adverse events or death in affected subjects. As referred to herein, a major adverse event is one that can occur anywhere within the body due to the presence of a vascular lesion. Major adverse events can include, but are not limited to, major adverse cardiac events, major adverse events in the peripheral or central vasculature, major adverse events in the brain, major adverse events in the musculature, or major adverse events in any of the internal organs.

In various embodiments, the catheter systems and related methods disclosed herein can include a catheter configured to advance to a vascular lesion, such as a calcified vascular lesion or a fibrous vascular lesion, at a treatment site located within or adjacent a blood vessel within a body of a patient. The catheter includes a catheter shaft, and an inflatable balloon that is coupled and/or secured to the catheter shaft. The balloon can include a balloon wall that defines a balloon interior. The balloon can be configured to receive a catheter fluid within the balloon interior to expand from a deflated state suitable for advancing the catheter through a patient's vasculature, to an inflated state suitable for anchoring the catheter in position relative to the treatment site.

As used herein, the terms "treatment site", "intravascular lesion" and "vascular lesion" are used interchangeably unless otherwise noted. As such, the intravascular lesions and/or the vascular lesions are sometimes referred to herein simply as "lesions."

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings. The same or similar nomenclature and/or reference indicators will be used throughout the drawings and the following detailed description to refer to the same or like parts.

In the interest of clarity, not all of the routine features of the implementations described herein are shown and described. It is appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is recognized that such a development effort might be complex and time-consuming, but would nevertheless be a routine undertaking of engineering for those of ordinary skill in the art having the benefit of this disclosure.

The catheter systems disclosed herein can include many different forms. Referring now to FIG. 1, a simplified schematic cross-sectional view illustration is shown of a catheter system 100 in accordance with various embodiments. The catheter system 100 is suitable for imparting pressure waves to induce fractures in one or more vascular lesions within or adjacent a vessel wall of a blood vessel or on or adjacent to a heart valve within a body of a patient. In the embodiment illustrated in FIG. 1, the catheter system 100 can include one or more of a catheter 102, an energy guide bundle 122 including one or more energy guides 122A, a fluid pump 138, a system console 123 including one or more of an energy source 124, a power source 125, a system controller 126, a graphic user interface 127 (a "GUI"), and a handle assembly 128 that includes a source manifold 136 integrated therein. Alternatively, the catheter system 100 can include more components or fewer components than those specifically illustrated and described in relation to FIG. 1.

The catheter 102 is configured to move to the treatment site 106 within or adjacent to a vessel wall 108A of a blood vessel 108 within a body 107 of a patient 109. The treatment site 106 can include one or more vascular lesions 106A such as calcified vascular lesions, for example. Additionally, or in the alternative, the treatment site 106 can include vascular lesions 106A such as fibrous vascular lesions. Still alternatively, in some implementations, the catheter 102 can be used at a treatment site 106 within or adjacent to a heart valve within the body 107 of the patient 109.

The catheter 102 can include an inflatable balloon 104 (sometimes referred to herein simply as a "balloon"), a catheter shaft 110, and a guidewire 112. The balloon 104 can be coupled to the catheter shaft 110. The balloon 104 can include a balloon proximal end 104P and a balloon distal end 104D. The catheter shaft 110 can extend from a proximal portion 114 of the catheter system 100 to a distal portion 116 of the catheter system 100. The catheter shaft 110 can include a longitudinal axis 144. The catheter 102 and/or the catheter shaft 110 can also include a guidewire lumen 118 which is configured to move over the guidewire 112. As utilized herein, the guidewire lumen 118 defines a conduit through which the guidewire 112 extends. The catheter shaft 110 can further include an inflation lumen (not shown) and/or various other lumens for various other purposes. In some embodiments, the catheter 102 can have a distal end opening 120 and can accommodate and be tracked over the guidewire 112 as the catheter 102 is moved and positioned at or near the treatment site 106. In some embodiments, the balloon proximal end 104P can be coupled to the catheter shaft 110, and the balloon distal end 104D can be coupled to the guidewire lumen 118.

The balloon 104 includes a balloon wall 130 that defines a balloon interior 146. The balloon 104 can be selectively inflated with a catheter fluid 132 to expand from a deflated state suitable for advancing the catheter 102 through a patient's vasculature, to an inflated state (as shown in FIG. 1) suitable for anchoring the catheter 102 in position relative to the treatment site 106. Stated in another manner, when the balloon 104 is in the inflated state, the balloon wall 130 of the balloon 104 is configured to be positioned substantially adjacent to the treatment site 106. It is appreciated that although FIG. 1 illustrates the balloon wall 130 of the balloon 104 being shown spaced apart from the treatment site 106 of the blood vessel 108 when in the inflated state, this is done for ease of illustration. It is recognized that the balloon wall 130 of the balloon 104 will typically be substantially directly adjacent to and/or abutting the treatment site 106 when the balloon 104 is in the inflated state.

The balloon 104 suitable for use in the catheter system 100 includes those that can be passed through the vasculature of a patient 109 when in the deflated state. In some embodiments, the balloons 104 are made from silicone. In other embodiments, the balloon 104 can be made from materials such as polydimethylsiloxane (PDMS), polyurethane, polymers such as PEBAX™ material, nylon, or any other suitable material.

The balloon 104 can have any suitable diameter (in the inflated state). In various embodiments, the balloon 104 can have a diameter (in the inflated state) ranging from less than one millimeter (mm) up to 25 mm. In some embodiments, the balloon 104 can have a diameter (in the inflated state) ranging from at least 1.5 mm up to 14 mm. In some embodiments, the balloon 104 can have a diameter (in the inflated state) ranging from at least two mm up to five mm.

In some embodiments, the balloon 104 can have a length ranging from at least three mm to 300 mm. More particularly, in some embodiments, the balloon 104 can have a length ranging from at least eight mm to 200 mm. It is appreciated that a balloon 104 having a relatively longer length can be positioned adjacent to larger treatment sites 106, and, thus, may be usable for imparting pressure waves onto and inducing fractures in larger vascular lesions 106A or multiple vascular lesions 106A at precise locations within the treatment site 106. It is further appreciated that a longer balloon 104 can also be positioned adjacent to multiple treatment sites 106 at any one given time.

The balloon 104 can be inflated to inflation pressures of between approximately one atmosphere (atm) and 70 atm. In some embodiments, the balloon 104 can be inflated to inflation pressures of from at least 20 atm to 60 atm. In other embodiments, the balloon 104 can be inflated to inflation pressures of from at least six atm to 20 atm. In still other embodiments, the balloon 104 can be inflated to inflation pressures of from at least three atm to 20 atm. In yet other embodiments, the balloon 104 can be inflated to inflation pressures of from at least two atm to ten atm.

The balloon 104 can have various shapes, including, but not to be limited to, a conical shape, a square shape, a rectangular shape, a spherical shape, a conical/square shape, a conical/spherical shape, an extended spherical shape, an oval shape, a tapered shape, a bone shape, a stepped diameter shape, an offset shape, or a conical offset shape. In some embodiments, the balloon 104 can include a drug eluting coating or a drug eluting stent structure. The drug eluting coating or drug eluting stent can include one or more therapeutic agents including anti-inflammatory agents, anti-neoplastic agents, anti-angiogenic agents, and the like.

The catheter fluid 132 can be a liquid or a gas. Some examples of the catheter fluid 132 suitable for use can include, but are not limited to one or more of water, saline, contrast medium, fluorocarbons, perfluorocarbons, gases, such as carbon dioxide, or any other suitable catheter fluid 132. In some embodiments, the catheter fluid 132 can be used as a base inflation fluid. In some embodiments, the catheter fluid 132 can include a mixture of saline to contrast medium in a volume ratio of approximately 50:50. In other embodiments, the catheter fluid 132 can include a mixture of saline to contrast medium in a volume ratio of approximately 25:75. In still other embodiments, the catheter fluid 132 can include a mixture of saline to contrast medium in a volume ratio of approximately 75:25. However, it is understood that any suitable ratio of saline to contrast medium can be used. The catheter fluid 132 can be tailored on the basis of composition, viscosity, and the like so that the rate of travel of the pressure waves are appropriately manipulated. In certain embodiments, the catheter fluids 132 suitable for use are biocompatible. A volume of catheter fluid 132 can be tailored by the chosen energy source 124 and the type of catheter fluid 132 used.

In some embodiments, the contrast agents used in the contrast media can include, but are not to be limited to, iodine-based contrast agents, such as ionic or non-ionic iodine-based contrast agents. Some non-limiting examples of ionic iodine-based contrast agents include diatrizoate, metrizoate, iothalamate, and ioxaglate. Some non-limiting examples of non-ionic iodine-based contrast agents include iopamidol, iohexol, ioxilan, iopromide, iodixanol, and ioversol. In other embodiments, non-iodine-based contrast agents can be used. Suitable non-iodine containing contrast agents can include gadolinium (III)-based contrast agents. Suitable fluorocarbon and perfluorocarbon agents can include, but are not to be limited to, agents such as the perfluorocarbon dodecafluoropentane (DDFP, C5F12).

The catheter fluids 132 can include those that include absorptive agents that can selectively absorb light in the ultraviolet region (e.g., at least ten nanometers (nm) to 400 nm), the visible region (e.g., at least 400 nm to 780 nm), or the near-infrared region (e.g., at least 780 nm to 2.5 μm) of the electromagnetic spectrum. Suitable absorptive agents can include those with absorption maxima along the spectrum from at least ten nm to 2.5 μm. Alternatively, the catheter fluids 132 can include those that include absorptive agents that can selectively absorb light in the mid-infrared region (e.g., at least 2.5 μm to 15 μm), or the far-infrared region (e.g., at least 15 μm to one mm) of the electromagnetic spectrum. In various embodiments, the absorptive agent can be those that have an absorption maximum matched with the emission maximum of the laser used in the catheter system 100. By way of non-limiting examples, various lasers usable in the catheter system 100 can include neodymium:yttrium-aluminum-garnet (Nd:YAG–emission maximum=1064 nm) lasers, holmium:YAG (Ho:YAG–emission maximum=2.1 μm) lasers, or erbium:YAG (Er:YAG–emission maximum=2.94 μm) lasers. In some embodiments, the absorptive agents can be water-soluble. In other embodiments, the absorptive agents are not water-soluble. In some embodiments, the absorptive agents used in the catheter fluids 132 can be tailored to match the peak emission of the energy source 124. Various energy sources 124 having emission wavelengths of at least ten nanometers to one millimeter are discussed elsewhere herein.

The catheter shaft 110 of the catheter 102 can be coupled to the one or more energy guides 122A of the energy guide bundle 122 that are in optical communication with the energy source 124. The energy guide(s) 122A can be disposed along the catheter shaft 110 and within the balloon 104. In some embodiments, each energy guide 122A can be an optical fiber and the energy source 124 can be a laser. The energy source 124 can be in optical communication with the energy guides 122A at the proximal portion 114 of the catheter system 100.

In some embodiments, the catheter shaft 110 can be coupled to multiple energy guides 122A such as a first energy guide, a second energy guide, a third energy guide, etc., which can be disposed at any suitable positions about and/or relative to the guidewire lumen 118 and/or the catheter shaft 110. For example, in certain non-exclusive embodiments, two energy guides 122A can be spaced apart by approximately 180 degrees about the circumference of the guidewire lumen 118 and/or the catheter shaft 110; three energy guides 122A can be spaced apart by approximately 120 degrees about the circumference of the guidewire lumen 118 and/or the catheter shaft 110; four energy guides 122A can be spaced apart by approximately 90 degrees about the circumference of the guidewire lumen 118 and/or the catheter shaft 110; six energy guides 122A can be spaced apart by approximately 60 degrees about the circumference of the guidewire lumen 118 and/or the catheter shaft 110; eight energy guides 122A can be spaced apart by approximately 45 degrees about the circumference of the guidewire lumen 118 and/or the catheter shaft 110; or ten energy guides 122A can be spaced apart by approximately 36 degrees about the circumference of the guidewire lumen 118 and/or the catheter shaft 110. Still alternatively, multiple energy guides 122A need not be uniformly spaced apart from one another about the circumference of the guidewire lumen 118 and/or the catheter shaft 110. More particularly, it is further appreciated that the energy guides 122A can be disposed uniformly or non-uniformly about the guidewire lumen 118 and/or the catheter shaft 110 to achieve the desired effect in the desired locations.

The catheter system 100 and/or the energy guide bundle 122 can include any number of energy guides 122A in optical communication with the energy source 124 at the proximal portion 114, and with the catheter fluid 132 within the balloon interior 146 of the balloon 104 at the distal portion 116. For example, in some embodiments, the catheter system 100 and/or the energy guide bundle 122 can include from one energy guide 122A to greater than 30 energy guides 122A. Alternatively, in other embodiments, the catheter system 100 and/or the energy guide bundle 122 can include greater than 30 energy guides 122A.

The energy guides 122A can have any suitable design for purposes of generating plasma and/or pressure waves in the catheter fluid 132 within the balloon interior 146. Thus, the general description of the energy guides 122A as light guides is not intended to be limiting in any manner, except for as set forth in the claims appended hereto. More particularly, although the catheter systems 100 are often described with the energy source 124 as a light source and the one or more energy guides 122A as light guides, the catheter system 100 can alternatively include any suitable energy source 124 and energy guides 122A for purposes of generating the desired plasma in the catheter fluid 132 within the balloon interior 146. For example, in one non-exclusive alternative embodiment, the energy source 124 can be configured to provide high voltage pulses, and each energy guide 122A can include an electrode pair including spaced apart electrodes that extend into the balloon interior 146. In such embodiment, each pulse of high voltage is applied to the electrodes and forms an electrical arc across the electrodes, which, in turn, generates the plasma and forms the pressure waves in the catheter fluid 132 that are utilized to provide the fracture force onto the vascular lesions 106A at the treatment site

106. Still alternatively, the energy source 124 and/or the energy guides 122A can have another suitable design and/or configuration.

In certain embodiments, the energy guides 122A can include an optical fiber or flexible light pipe. The energy guides 122A can be thin and flexible and can allow light signals to be sent with very little loss of strength. The energy guides 122A can include a core surrounded by a cladding about its circumference. In some embodiments, the core can be a cylindrical core or a partially cylindrical core. The core and cladding of the energy guides 122A can be formed from one or more materials, including but not limited to one or more types of glass, silica, or one or more polymers. The energy guides 122A may also include a protective coating, such as a polymer. It is appreciated that the index of refraction of the core will be greater than the index of refraction of the cladding.

Each energy guide 122A can guide energy along its length from a guide proximal end 122P to the guide distal end 122D having at least one optical window (not shown) that is positioned within the balloon interior 146.

The energy guides 122A can assume many configurations about and/or relative to the catheter shaft 110 of the catheter 102. In some embodiments, the energy guides 122A can run parallel to the longitudinal axis 144 of the catheter shaft 110. In some embodiments, the energy guides 122A can be physically coupled to the catheter shaft 110. In other embodiments, the energy guides 122A can be disposed along a length of an outer diameter of the catheter shaft 110. In yet other embodiments, the energy guides 122A can be disposed within one or more energy guide lumens within the catheter shaft 110.

The energy guides 122A can also be disposed at any suitable positions about the circumference of the guidewire lumen 118 and/or the catheter shaft 110, and the guide distal end 122D of each of the energy guides 122A can be disposed at any suitable longitudinal position relative to the length of the balloon 104 and/or relative to the length of the guidewire lumen 118 to more effectively and precisely impart pressure waves for purposes of disrupting the vascular lesions 106A at the treatment site 106.

In certain embodiments, the energy guides 122A can include one or more photoacoustic transducers 154, where each photoacoustic transducer 154 can be in optical communication with the energy guide 122A within which it is disposed. In some embodiments, the photoacoustic transducers 154 can be in optical communication with the guide distal end 122D of the energy guide 122A. In such embodiments, the photoacoustic transducers 154 can have a shape that corresponds with and/or conforms to the guide distal end 122D of the energy guide 122A.

The photoacoustic transducer 154 is configured to convert light energy into an acoustic wave at or near the guide distal end 122D of the energy guide 122A. The direction of the acoustic wave can be tailored by changing an angle of the guide distal end 122D of the energy guide 122A.

In certain embodiments, the photoacoustic transducers 154 disposed at the guide distal end 122D of the energy guide 122A can assume the same shape as the guide distal end 122D of the energy guide 122A. For example, in certain non-exclusive embodiments, the photoacoustic transducer 154 and/or the guide distal end 122D can have a conical shape, a convex shape, a concave shape, a bulbous shape, a square shape, a stepped shape, a half-circle shape, an ovoid shape, and the like. The energy guide 122A can further include additional photoacoustic transducers 154 disposed along one or more side surfaces of the length of the energy guide 122A.

In some embodiments, the energy guides 122A can further include one or more diverting features or "diverters" (not shown in FIG. 1), such as within the energy guide 122A and/or near the guide distal end 122D of the energy guide 122A, that are configured to direct energy from the energy guide 122A toward a side surface which can be located at or near the guide distal end 122D of the energy guide 122A, before the energy is directed toward the balloon wall 130. A diverting feature can include any feature of the system that diverts energy from the energy guide 122A away from its axial path toward a side surface of the energy guide 122A. The energy guides 122A can each include one or more optical windows disposed along the longitudinal or circumferential surfaces of each energy guide 122A and in optical communication with a diverting feature. Stated in another manner, the diverting features can be configured to direct energy in the energy guide 122A toward a side surface that is at or near the guide distal end 122D, where the side surface is in optical communication with an optical window. The optical windows can include a portion of the energy guide 122A that allows energy to exit the energy guide 122A from within the energy guide 122A, such as a portion of the energy guide 122A lacking a cladding material on or about the energy guide 122A.

Examples of the diverting features suitable for use include a reflecting element, a refracting element, and a fiber diffuser. The diverting features suitable for focusing energy away from the tip of the energy guides 122A can include, but are not to be limited to, those having a convex surface, a gradient-index (GRIN) lens, and a mirror focus lens. Upon contact with the diverting feature, the energy is diverted within the energy guide 122A to one or more of a plasma generator 133 and the photoacoustic transducer 154 that is in optical communication with a side surface of the energy guide 122A. When utilized, the photoacoustic transducer 154 then converts light energy into an acoustic wave that extends away from the side surface of the energy guide 122A.

As noted above, in the embodiment illustrated in FIG. 1, the system console 123 includes one or more of the energy source 124, the power source 125, the system controller 126, and the GUI 127. Alternatively, the system console 123 can include more components or fewer components than those specifically illustrated in FIG. 1. For example, in certain non-exclusive alternative embodiments, the system console 123 can be designed without the GUI 127. Still alternatively, one or more of the energy source 124, the power source 125, the system controller 126, and the GUI 127 can be provided at any suitable location within the catheter system 100 without the specific need for the system console 123.

As shown, the system console 123, and the components included therewith, is operatively coupled to the catheter 102, the energy guide bundle 122, and the remainder of the catheter system 100. For example, in some embodiments, as illustrated in FIG. 1, the system console 123 can include a console connection aperture 148 (also sometimes referred to generally as a "socket") by which the energy guide bundle 122 is mechanically coupled to the system console 123. In such embodiments, the energy guide bundle 122 can include a guide coupling housing 150 (also sometimes referred to generally as a "ferrule") that houses a portion, such as the guide proximal end 122P, of each of the energy guides 122A. The guide coupling housing 150 is configured to fit and be selectively retained within the console connection aperture

148 to provide the mechanical coupling between the energy guide bundle 122 and the system console 123.

The energy guide bundle 122 can also include a guide bundler 152 (or "shell") that brings each of the individual energy guides 122A closer together so that the energy guides 122A and/or the energy guide bundle 122 can be in a more compact form as it extends with the catheter 102 into the blood vessel 108 during use of the catheter system 100.

The energy source 124 can be selectively and/or alternatively coupled in optical communication with each of the energy guides 122A, such as to the guide proximal end 122P of each of the energy guides 122A, in the energy guide bundle 122. In particular, the energy source 124 is configured to generate energy in the form of a source beam 124A, such as a pulsed source beam, that can be selectively and/or alternatively directed to and received by each of the energy guides 122A in the energy guide bundle 122 as an individual guide beam 124B. Alternatively, the catheter system 100 can include more than one energy source 124. For example, in one non-exclusive alternative embodiment, the catheter system 100 can include a separate energy source 124 for each of the energy guides 122A in the energy guide bundle 122.

The energy source 124 can have any suitable design. In certain embodiments, the energy source 124 can be configured to provide sub-millisecond pulses of energy from the energy source 124 that are focused onto a small spot in order to couple it into the guide proximal end 122P of the energy guide 122A. Such pulses of energy are then directed and/or guided along the energy guides 122A to a location within the balloon interior 146 of the balloon 104, thereby inducing plasma formation in the catheter fluid 132 within the balloon interior 146 of the balloon 104, such as via the plasma generator 133 that can be located at or near the guide distal end 122D of the energy guide 122A. In particular, in such embodiments, the energy emitted at the guide distal end 122D of the energy guide 122A is directed toward and energizes the plasma generator 133 to form the plasma in the catheter fluid 132 within the balloon interior 146. The plasma formation causes rapid bubble formation, and imparts pressure waves upon the treatment site 106. An exemplary plasma-induced bubble 134 is illustrated in FIG. 1.

In various non-exclusive alternative embodiments, the sub-millisecond pulses of energy from the energy source 124 can be delivered to the treatment site 106 at a frequency of between approximately one hertz (Hz) and 5000 Hz, between approximately 30 Hz and 1000 Hz, between approximately ten Hz and 100 Hz, or between approximately one Hz and 30 Hz. Alternatively, the sub-millisecond pulses of energy can be delivered to the treatment site 106 at a frequency that can be greater than 5000 Hz or less than one Hz, or any other suitable range of frequencies.

It is appreciated that although the energy source 124 is typically utilized to provide pulses of energy, the energy source 124 can still be described as providing a single source beam 124A, i.e. a single pulsed source beam.

The energy sources 124 suitable for use can include various types of light sources including lasers and lamps. Alternatively, the energy sources 124 can include any suitable type of energy source.

Suitable lasers can include short pulse lasers on the sub-millisecond timescale. In some embodiments, the energy source 124 can include lasers on the nanosecond (ns) timescale. The lasers can also include short pulse lasers on the picosecond (ps), femtosecond (fs), and microsecond (us) timescales. It is appreciated that there are many combinations of laser wavelengths, pulse widths and energy levels that can be employed to achieve plasma in the catheter fluid 132 of the catheter 102. In various non-exclusive alternative embodiments, the pulse widths can include those falling within a range including from at least ten ns to 3000 ns, at least 20 ns to 100 ns, or at least one ns to 500 ns. Alternatively, any other suitable pulse width range can be used.

Exemplary nanosecond lasers can include those within the UV to IR spectrum, spanning wavelengths of about ten nanometers (nm) to one millimeter (mm). In some embodiments, the energy sources 124 suitable for use in the catheter systems 100 can include those capable of producing light at wavelengths of from at least 750 nm to 2000 nm. In other embodiments, the energy sources 124 can include those capable of producing light at wavelengths of from at least 700 nm to 3000 nm. In still other embodiments, the energy sources 124 can include those capable of producing light at wavelengths of from at least 100 nm to ten micrometers (μm). Nanosecond lasers can include those having repetition rates of up to 200 kHz.

In some embodiments, the laser can include a Q-switched thulium:yttrium-aluminum-garnet (Tm:YAG) laser. In other embodiments, the laser can include a neodymium:yttrium-aluminum-garnet (Nd:YAG) laser, holmium:yttrium-aluminum-garnet (Ho:YAG) laser, erbium:yttrium-aluminum-garnet (Er:YAG) laser, excimer laser, helium-neon laser, carbon dioxide laser, as well as doped, pulsed, fiber lasers.

In still other embodiments, the energy source 124 can include a plurality of lasers that are grouped together in series. In yet other embodiments, the energy source 124 can include one or more low energy lasers that are fed into a high energy amplifier, such as a master oscillator power amplifier (MOPA). In still yet other embodiments, the energy source 124 can include a plurality of lasers that can be combined in parallel or in series to provide the energy needed to create the plasma bubble 134 in the catheter fluid 132.

The catheter system 100 can generate pressure waves having maximum pressures in the range of at least one megapascal (MPa) to 100 MPa. The maximum pressure generated by a particular catheter system 100 will depend on the energy source 124, the absorbing material, the bubble expansion, the propagation medium, the balloon material, and other factors. In various non-exclusive alternative embodiments, the catheter systems 100 can generate pressure waves having maximum pressures in the range of at least approximately two MPa to 50 MPa, at least approximately two MPa to 30 MPa, or approximately at least 15 MPa to 25 MPa.

The pressure waves can be imparted upon the treatment site 106 from a distance within a range from at least approximately 0.1 millimeters (mm) to greater than approximately 25 mm extending radially from the energy guides 122A when the catheter 102 is placed at the treatment site 106. In various non-exclusive alternative embodiments, the pressure waves can be imparted upon the treatment site 106 from a distance within a range from at least approximately ten mm to 20 mm, at least approximately one mm to ten mm, at least approximately 1.5 mm to four mm, or at least approximately 0.1 mm to ten mm extending radially from the energy guides 122A when the catheter 102 is placed at the treatment site 106. In other embodiments, the pressure waves can be imparted upon the treatment site 106 from another suitable distance that is different than the foregoing ranges. In some embodiments, the pressure waves can be imparted upon the treatment site 106 within a range of at least approximately two MPa to 30 MPa at a distance from at least approximately 0.1 mm to ten mm. In some embodiments, the pressure waves can be imparted upon the treatment site 106 from a range of at least approximately two MPa to 25 MPa at a distance from at least approximately 0.1 mm to ten mm. Still alternatively, other suitable pressure ranges and distances can be used.

The power source 125 is electrically coupled to and is configured to provide necessary power to each of the energy source 124, the system controller 126, the GUI 127, and the handle assembly 128. The power source 125 can have any suitable design for such purposes.

The system controller 126 is electrically coupled to and receives power from the power source 125. The system controller 126 is coupled to and is configured to control operation of each of the energy source 124 and the GUI 127. The system controller 126 can include one or more processors or circuits for purposes of controlling the operation of at least the energy source 124 and the GUI 127. For example, the system controller 126 can control the energy source 124 for generating pulses of energy as desired and/or at any desired firing rate.

The system controller 126 can also be configured to control operation of other components of the catheter system 100 such as the positioning of the catheter 102 adjacent to the treatment site 106, the inflation of the balloon 104 with the catheter fluid 132, etc. Further, or in the alternative, the catheter system 100 can include one or more additional controllers that can be positioned in any suitable manner for purposes of controlling the various operations of the catheter system 100. For example, in certain embodiments, an additional controller and/or a portion of the system controller 126 can be positioned and/or incorporated within the handle assembly 128.

The GUI 127 is accessible by the user or operator of the catheter system 100. The GUI 127 is electrically connected to the system controller 126. With such design, the GUI 127 can be used by the user or operator to ensure that the catheter system 100 is effectively utilized to impart pressure onto and induce fractures into the vascular lesions 106A at the treatment site 106. The GUI 127 can provide the user or operator with information that can be used before, during and after use of the catheter system 100. In one embodiment, the GUI 127 can provide static visual data and/or information to the user or operator. In addition, or in the alternative, the GUI 127 can provide dynamic visual data and/or information to the user or operator, such as video data or any other data that changes over time during use of the catheter system 100. In various embodiments, the GUI 127 can include one or more colors, different sizes, varying brightness, etc., that may act as alerts to the user or operator. Additionally, or in the alternative, the GUI 127 can provide audio data or information to the user or operator. The specifics of the GUI 127 can vary depending upon the design requirements of the catheter system 100, or the specific needs, specifications and/or desires of the user or operator.

As shown in FIG. 1, the handle assembly 128 can be positioned at or near the proximal portion 114 of the catheter system 100. In this embodiment, the handle assembly 128 is coupled to the balloon 104 and is positioned spaced apart from the balloon 104. Alternatively, the handle assembly 128 can be positioned at another suitable location.

The handle assembly 128 is attached to the catheter shaft 110 and is handled and used by the user or operator to operate, position and control the catheter 102. The design and specific features of the handle assembly 128 can vary to suit the design requirements of the catheter system 100. In the embodiment illustrated in FIG. 1, the handle assembly 128 is separate from, but in electrical and/or fluid communication with one or more of the system controller 126, the energy source 124, the fluid pump 138, and the GUI 127.

In some embodiments, the handle assembly 128 can integrate and/or include at least a portion of the system controller 126 within an interior of the handle assembly 128. For example, as shown, in certain such embodiments, the handle assembly 128 can include circuitry 156, which is electrically coupled between catheter electronics and the system console 123, and which can form at least a portion of the system controller 126. In one embodiment, the circuitry 156 can include a printed circuit board having one or more integrated circuits, or any other suitable circuitry. In an alternative embodiment, the circuitry 156 can be omitted, or can be included within the system controller 126, which in various embodiments can be positioned outside of the handle assembly 128, such as within the system console 123. It is understood that the handle assembly 128 can include fewer or additional components than those specifically illustrated and described herein.

Further included with the handle assembly 128 is an energy activation member 157 (also sometimes referred to herein simply as an "energy activator"), such as an energy activation button, that can be coupled to the circuitry 156 within the handle assembly 128 which forms a part of the system controller 126. The energy activator 157 is configured to enable the user or operator to selectively activate the catheter system 100 as desired.

In various embodiments, as noted above, the source manifold 136 can be integrated and/or incorporated within the handle assembly 128, and can positioned at or near the proximal portion 114 of the catheter system 100. As shown, the source manifold 136 can include one or more openings that can receive an inflation conduit 140 that is coupled in fluid communication with the fluid pump 138, the guidewire 112 and/or the guidewire lumen 118, one or more energy guides 122A of the energy guide bundle 122, and/or the catheter shaft 110. More particularly, the source manifold 136 can include one or more of a media inflation port 158, a guidewire lumen port 160, an energy guide port 162, and a catheter shaft port 164.

The catheter system 100 can also include the fluid pump 138 that is configured to inflate the balloon 104 with the catheter fluid 132 as needed.

Various embodiments of the source manifold 136, and the specific components included therewith, are illustrated and described in detail herein below within subsequent Figures.

As with all embodiments illustrated and described herein, various structures may be omitted from the figures for clarity and ease of understanding. Further, the figures may include certain structures that can be omitted without deviating from the intent and scope of the invention.

Figure 2:
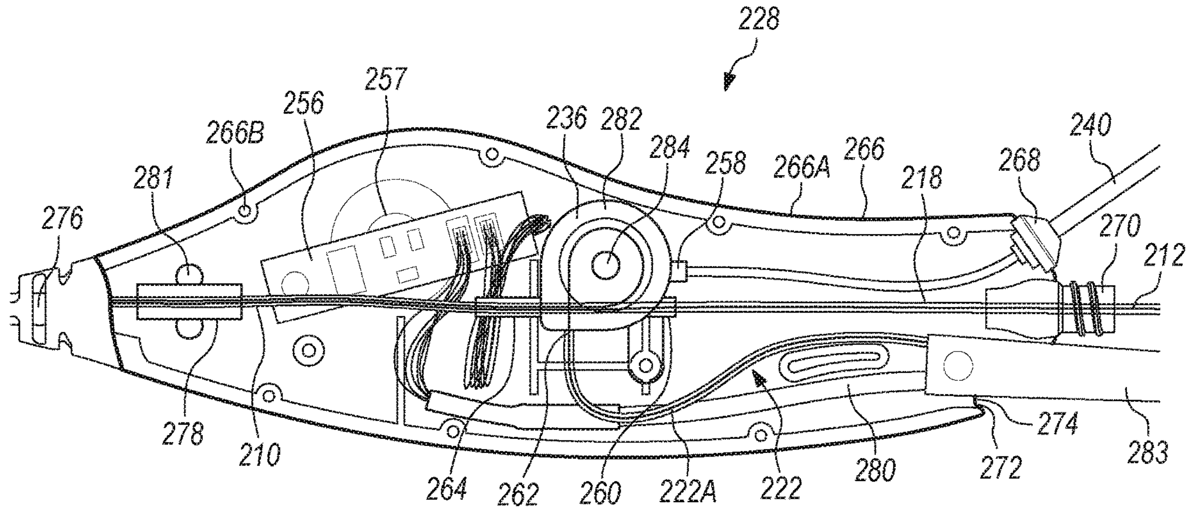
FIG. 2 is a simplified cutaway view illustration of an embodiment of the handle assembly of FIG. 1.

FIG. 2 is a simplified cutaway view illustration of an embodiment of the handle assembly 228. The design of the handle assembly 228 and the various components retained therein can be varied to suit the requirements of the catheter system 100 (illustrated in FIG. 1). As illustrated in this embodiment, the handle assembly 228 can include an assembly housing 266 that includes and/or defines one or more of an inflation conduit inlet 268, a guidewire inlet 270, an energy guide inlet 272, an electrical inlet 274, a handle distal outlet 276, and a catheter shaft hub 278; circuitry 256 with an integrated energy activator 257; and a source manifold 236. Alternatively, the handle assembly 228 can include more components or fewer components than those specifically illustrated and described herein.

In some embodiments, the assembly housing 266 can be formed from two housing members 266A (only one of which is shown in FIG. 2) formed as a first housing side and a second housing side that are selectively coupled together to form the complete assembly housing 266. FIG. 2 further illustrates that the housing member 266A can include a plurality of coupling members 266B that are configured to engage corresponding coupling members on the other housing member 266A. In one embodiment, the coupling members 266B can include a series of pins and corresponding apertures that are configured to engage one another when the housing members 266A are being coupled together to form the complete assembly housing 266. Alternatively, the coupling members 266B can have another suitable design.

The inflation conduit inlet 268 is configured to couple the inflation conduit 240 into the assembly housing 266.

The guidewire inlet 270 is configured to couple the guidewire 212 into the assembly housing 266.

The energy guide inlet 272 is configured to couple the energy guide bundle 222 including the one or more energy guides 222A into the assembly housing 266.

The electrical inlet 274 is configured to couple an electrical cable 280 into the assembly housing 266.

As shown, it is appreciated that in certain embodiments, the energy guide inlet 272 and the electrical inlet 274 can be formed together into a single inlet. For example, in one embodiment, the energy guides 222A and the electrical cable 280 can be shrouded within an optical/electrical cable 283 as the energy guides 222A and the electrical cable 280 enter into the assembly housing 266 through the energy guide inlet 272 and the electrical inlet 274, respectively. Alternatively, the energy guide inlet 272 and the electrical inlet 274 can be formed independently of one another.

The handle distal outlet 276 provides an outlet from the assembly housing 266 for each of the inflation conduit 240, the guidewire 212, the guidewire lumen 218, the energy guide bundle 222, and the catheter shaft 210, as such components extend toward the balloon 104 (illustrated in FIG. 1).

The catheter shaft hub 278 is configured to support the catheter shaft 210 so that the catheter shaft 210 can be coupled into the handle distal outlet 276. In one embodiment, the catheter shaft hub 278 is adhered to the catheter shaft 210. In certain embodiments, the handle assembly 228 can further include locking features 281 that are configured to fix the catheter shaft hub 276 in place when the housing members 266A are coupled together to form the complete assembly housing 266.

The source manifold 236 is configured to help guide various components of the catheter 102 (illustrated in FIG. 1), such as the catheter shaft 210, the guidewire lumen 218, the guidewire 212, the energy guides 222A, and the inflation conduit 240, within the handle assembly 228 so that they can extend together to the balloon 104 (illustrated in FIG. 1).

The design of the source manifold 236 can be varied. As illustrated in FIG. 2, the source manifold 236 can include a manifold housing 282, and a pressure sensor 284 that is coupled to the manifold housing 282. In certain embodiments, the pressure sensor 284 is configured to sense a fluid pressure of the catheter fluid 132 (illustrated in FIG. 1) at one or more locations within the catheter system 100 (illustrated in FIG. 1). For example, in certain embodiments, the pressure sensor 284 can be configured to sense a fluid pressure of the catheter fluid 132 within the balloon interior 146 (illustrated in FIG. 1) or at any desired location along the inflation conduit 240. Alternatively, the pressure sensor 284 can be configured to sense a fluid pressure of the catheter fluid 132 at one or more other locations within the catheter system 100. In some non-exclusive embodiments, the pressure sensor 284 can be configured to sense the fluid pressure within the catheter fluid at any suitable locations up to approximately 10 atm, 15 atm, 20 atm, 25 atm, 30 atm, 35 atm, 40 atm, 45 atm, 50 atm, 55 atm, 60 atm, 65 atm, 70 atm, 75 atm, 80 atm, 85 atm, 90 atm, 95 atm, or 100 atm.

As above, the source manifold 236 can also include one or more of the media inflation port 258, the guidewire lumen port 260, the energy guide port 262, and the catheter shaft port 264 that can be coupled to and/or integrated into the manifold housing 282. In some embodiments, the energy guide bundle 222 and/or the one or more energy guides 222A can be coupled into the energy guide port 262 through use of a guide sealing component 585 (illustrated in FIG. 5). It is appreciated that the energy guide bundle 222 and/or the one or more energy guides 222A can be routed through the handle assembly 228 and/or the source manifold 236 in any suitable manner.

The circuitry 256 and the integrated energy activator 257 are substantially similar to what was illustrated and described herein above. More particularly, in some embodiments, the circuitry 256 can be provided in the form of a printed circuit board (PCB) that is attached to the pressure sensor 284 in the source manifold 236, and the energy activator 257 is integrated onto the circuitry 256 and is in electrical communication with the system console 123 (illustrated in FIG. 1) through the electrical cable 280.

Figure 3:
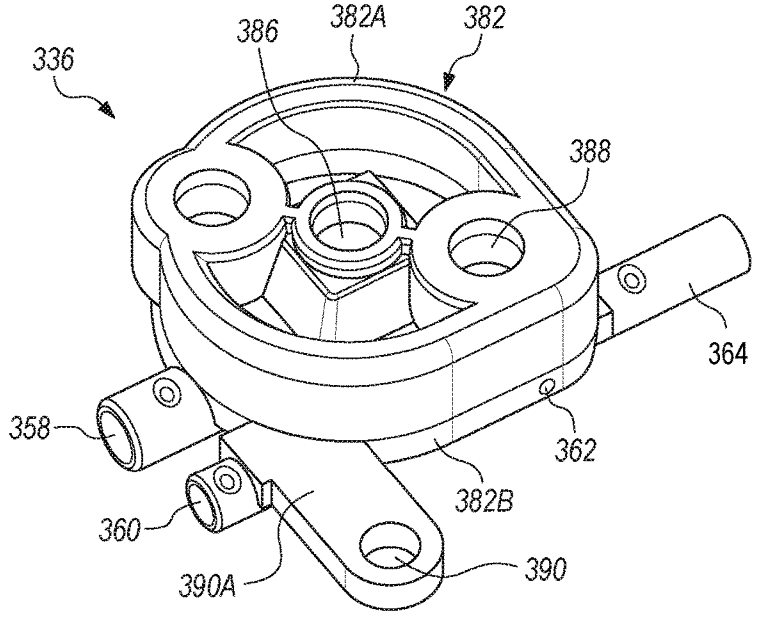
FIG. 3 is a simplified perspective view illustration of an embodiment of the source manifold of FIG. 1.

FIG. 3 is a simplified perspective view illustration of an embodiment of the source manifold 336. The design of the source manifold 336 can be varied to suit the requirements of the catheter system 100 (illustrated in FIG. 1). In various embodiments, as shown, the source manifold 336 can include a manifold housing 382 having a first housing member 382A and a second housing member 382B. In certain embodiments, the manifold housing 382 can include a sensor bore 386, one or more sensor controller attachment apertures 388 (two are shown in FIG. 3), at least one housing attachment aperture 390, the media inflation port 358, the guidewire lumen port 360, the energy guide port 362, and the catheter shaft port 364. Alternatively, the source manifold 336 and/or the manifold housing 382 can include more components or fewer components than what has been illustrated and described herein.

As shown, the first housing member 382A of the manifold housing 382 is selectively coupled to the second housing member 382B. The first housing member 382A and the second housing member 382B can be selectively coupled to one another in any suitable manner.

The sensor bore 386 is formed into the manifold housing 382, into the first housing member 382A in certain embodiments, and is configured to receive and retain the pressure sensor 284 (illustrated in FIG. 2). In some embodiments, the sensor bore 386 is substantially circular-shaped. Alternatively, the sensor bore 386 can be another suitable shape and/or can be positioned in another suitable manner.

The sensor controller attachment apertures 388 are usable to couple the circuitry 256 (illustrated in FIG. 2) to the source manifold 336 and/or the manifold housing 382. More particularly, in certain embodiments, a controller attacher (not shown), such as a screw or other suitable attacher, can extend through a portion of the circuitry 256 (or through another suitable device that is coupled to the circuitry 256) and can be received and retained in each of the sensor controller attachment apertures 388 to couple the circuitry 256 to the source manifold 336 and/or the manifold housing 382. In some embodiments, the source manifold 336 and/or the manifold housing 382 can include two sensor controller attachment apertures 388 that are positioned substantially adjacent to the sensor bore 386. In certain embodiments, the sensor controller attachment apertures 388 can be formed into the first housing member 382A of the manifold housing 382. Alternatively, the sensor controller attachment apertures 388 can have a different design and/or can be positioned in another suitable manner.

In one non-exclusive embodiment, an O-ring can be situated with grease against a wall within the sensor bore 386, and washers can be positioned between the circuitry 256, such as the PCB, and the manifold housing 382 of the source manifold 336 adjacent to the sensor controller attachment apertures 388.

The at least one housing attachment aperture 390 is usable for attaching the source manifold 336 to the assembly housing 266 (illustrated in FIG. 2) of the handle assembly 228 (illustrated in FIG. 2). More particularly, in certain embodiments, a manifold attacher (not shown), such as a screw or other suitable attacher, can extend through the at least one housing attachment aperture 390 and into an assembly aperture (not shown) formed into the assembly housing 266 of the handle assembly 228 to attach the source manifold 336 and/or the manifold housing 382 to the assembly housing 266. With such design, the source manifold 336 can be maintained in a desired position within the assembly housing 266 of the handle assembly 228.

In some embodiments, the housing attachment aperture 390 can be formed into an attachment arm 390A that cantilevers away from the second housing member 382B of the manifold housing 382. Alternatively, the at least one housing attachment aperture 390 can have a different design and/or be positioned in another suitable manner.

The design and general function of the media inflation port 358, the guidewire lumen port 360, the energy guide port 362, and the catheter shaft port 364 has been described in detail herein above. Accordingly, the media inflation port 358, the guidewire lumen port 360, the energy guide port 362, and the catheter shaft port 364 will not again be described in detail.

It is noted, however, that in one embodiment, each of the media inflation port 358, the guidewire lumen port 360, the energy guide port 362, and the catheter shaft port 364 are coupled to and/or formed into the second housing member 382B of the manifold housing 382. With this design, all lumens are kept on the same axis plane. Alternatively, one or more of the media inflation port 358, the guidewire lumen port 360, the energy guide port 362, and the catheter shaft port 364 can be coupled to and/or formed into the first housing member 382A of the manifold housing 382.

Figure 4:
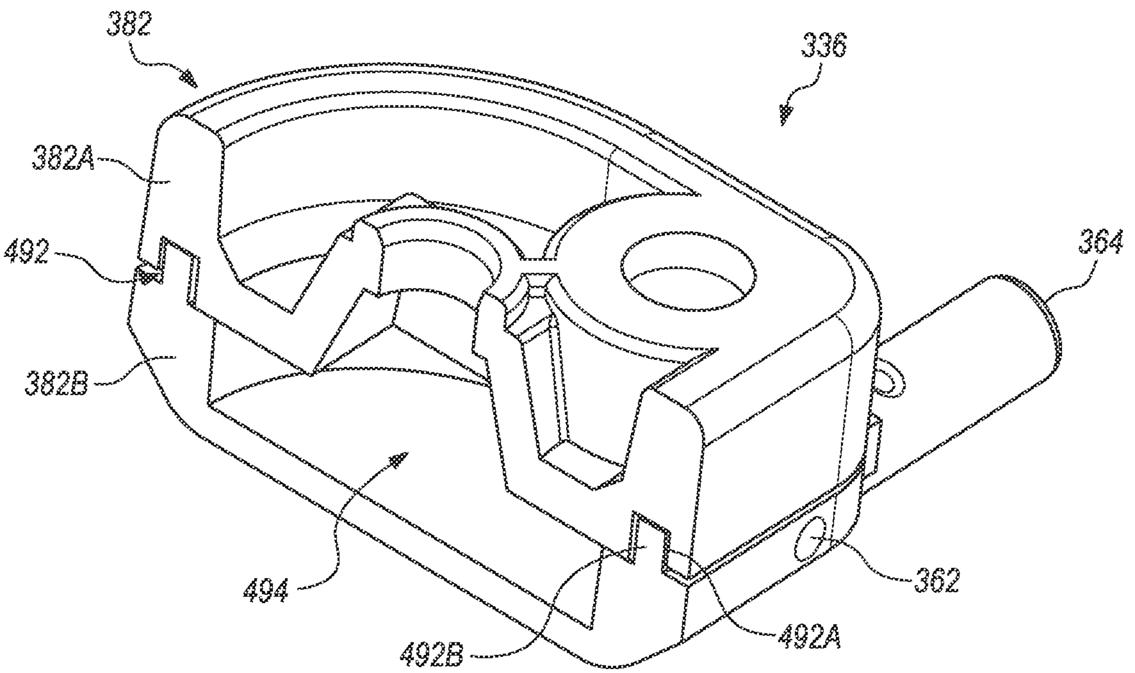
FIG. 4 is a simplified cutaway perspective view of a portion of the source manifold illustrated in FIG. 3.

FIG. 4 is a simplified cutaway perspective view of a portion of the source manifold 336 illustrated in FIG. 3. In particular, FIG. 4 is a simplified cutaway perspective view that shows the first housing member 382A of the manifold housing 382 being attached to the second housing member 382B.

It is appreciated that the attachment between the first housing member 382A and the second housing member 382B can be provided in any suitable manner. In certain embodiments, the attachment between the first housing member 382A and the second housing member 382B can be provided via an attachment assembly 492, which can include a first attachment member 492A that is coupled to and/or formed into the first housing member 382A, and a second attachment member 492B that is coupled to and/or formed into the second housing member 382B. In various embodiments, the first attachment member 492A is configured to selectively engage the second attachment member 492B as the first housing member 382A is being attached to the second housing member 382B. In one embodiment, as shown, the first attachment member 492A can include an attachment channel, and the second attachment member 492B can include an attachment projection that is configured to fit within the attachment channel of the first attachment member 492A. In another embodiment, the second attachment member 492B can include an attachment channel, and the first attachment member 492A can include an attachment projection that is configured to fit within the attachment channel of the second attachment member 492B. Alternatively, the first attachment member 492A and/or the second attachment member 492B can have another suitable design.

In alternative embodiments, the attachment between the first attachment member 492A and the second attachment member 492B can be secured in any suitable manner. For example, in one embodiment, an adhesive material can be used substantially adjacent to and/or between the first attachment member 492A and the second attachment member 492B, such as within the attachment channel. In another embodiment, the first attachment member 492A and the second attachment member 492B can be ultrasonically sealed to one another. In still another embodiment, the first attachment member 492A and the second attachment member 492B can be held together through friction fit. Alternatively, the first attachment member 492A and the second attachment member 492B can be secured together in another suitable manner.

FIG. 4 also illustrates that the first housing member 382A and the second housing member 382B of the manifold housing 382 define a media chamber 494 therebetween. In certain embodiments, it is desired that a volume of the media chamber 494 is minimized (in width and/or height) such that a volume of media within the media chamber 494 is minimized to allow for easier aspiration of the balloon 104 (illustrated in FIG. 1) during inflation. It is for this reason, in some embodiments, that the media inflation port 358 (illustrated in FIG. 3), the guidewire lumen port 360 (illustrated in FIG. 3), the energy guide port 362, and the catheter shaft port 364 are each coupled to and/or formed into the second housing member 382B of the manifold housing 382 to keep all lumens on the same axis plane.

As noted above, the energy guide port 362 is configured to couple the one or more energy guides 222A (illustrated in FIG. 2) of the energy guide bundle 222 (illustrated in FIG. 2) into and/or through the manifold housing 382, so that the energy guides 222A can guide energy from the energy source 124 (illustrated in FIG. 1), through the handle assembly 228 (illustrated in FIG. 2), and into the balloon interior 146 (illustrated in FIG. 1) of the balloon 104 (illustrated in FIG. 1).

It is appreciated that sealing a plurality of energy guides 222A, such as optical fibers or other suitable energy guides, into a single hole, such as the energy guide port 362, can be very challenging due to the small size of the energy guides. The number of energy guides 222A can also result in glue gaps as the energy guides 222A of the energy guide bundle 222 are coupled into the energy guide port 362. One way to solve this issue is to organize the energy guides 222A into individual channels of a multi-lumen extrusion as shown in FIG. 5.

Figure 5:
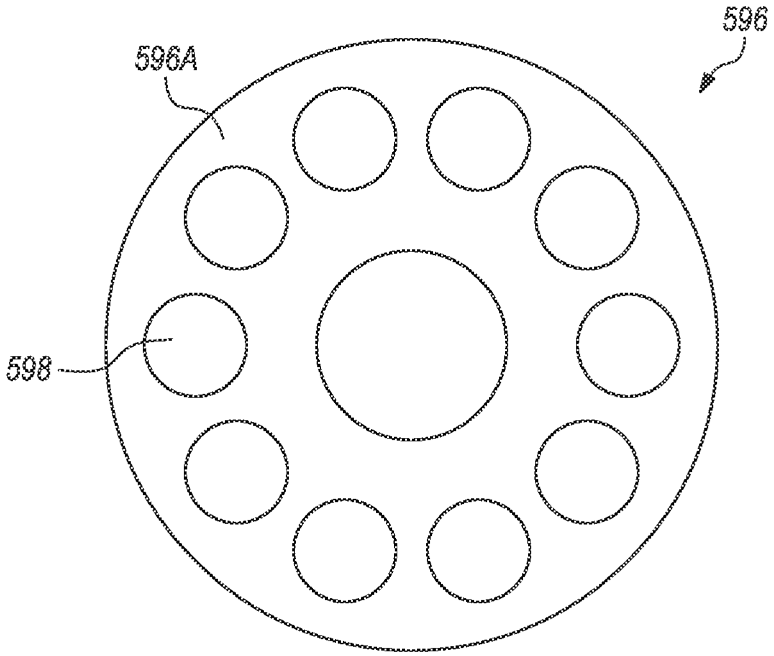
FIG. 5 is a simplified schematic view illustration of a multi-lumen optical sealing component that couples a plurality of energy guides into the source manifold of FIG. 3.

In particular, FIG. 5 is a simplified schematic view illustration of a multi-lumen optical sealing component 596 that is usable for coupling a plurality of energy guides 222A (illustrated in FIG. 2) into the source manifold 336 of FIG. 3, such as via the energy guide port 362 (illustrated in FIG. 3). In some embodiments, as shown, the optical sealing component 596 includes a seal body 596A that has a plurality of guide channels 598 formed therethrough.

In one embodiment, the seal body 596A can be substantially circular disk-shaped to match a substantially circular cross-section of the energy guide port 362 (illustrated in FIG. 3). Alternatively, the seal body 596A and/or the energy guide port 362 can have another suitable shape.

The number of guide channels 598 formed into and/or through the seal body 596A can be varied, and can be configured to suit the number of energy guides 222A included within the energy guide bundle 222 (illustrated in FIG. 2). In one embodiment, as shown in FIG. 5, the seal body 596A can include ten guide channels 598 to accommodate up to ten energy guides 222A. Alternatively, the seal body 596A can include greater than ten or less than ten guide channels 598.

In certain embodiments, once the energy guides 222A are all seated in their respective guide channels 598, the energy guides 222A can be reliably adhered to the optical sealing component 596 with a wicking adhesive. In one embodiment, the optical sealing component 596 and/or the seal body 596A can be formed from a transparent material so that UV glue can be used to promote curing. In one embodiment, the optical sealing component 596 and/or the seal body 596A can be adhered as a subassembly prior to bonding into the energy guide port 362 in the source manifold 336 (illustrated in FIG. 3).

In certain embodiments, the catheter systems and related methods utilize an energy source, e.g., a light source such as a laser source or another suitable energy source, which provides energy that is guided by one or more energy guides, e.g., light guides such as optical fibers, which are disposed along the catheter shaft and within the balloon interior of the balloon to create a localized plasma in the catheter fluid that is retained within the balloon interior of the balloon. The energy guide can be used in conjunction with a plasma generator that is positioned at or near a guide distal end of the energy guide within the balloon interior of the balloon located at the treatment site. The creation of the localized plasma can initiate a pressure wave and can initiate the rapid formation of one or more bubbles that can rapidly expand to a maximum size and then dissipate through a cavitation event that can launch a pressure wave upon collapse. The rapid expansion of the plasma-induced bubbles can generate one or more pressure waves in the catheter fluid retained within the balloon interior of the balloon and thereby impart pressure waves onto and induce fractures in the vascular lesions at the treatment site within or adjacent to the blood vessel wall within the body of the patient. In some embodiments, the energy source can be configured to provide sub-millisecond pulses of energy, e.g., light energy, to initiate the plasma formation in the catheter fluid within the balloon to cause the rapid bubble formation and to impart the pressure waves upon the balloon wall at the treatment site. Thus, the pressure waves can transfer mechanical energy through an incompressible catheter fluid to the treatment site to impart a fracture force on the intravascular lesion. Without wishing to be bound by any particular theory, it is believed that the rapid change in catheter fluid momentum upon the balloon wall that is in contact with the intravascular lesion is transferred to the intravascular lesion to induce fractures to the lesion.

The catheter systems and related methods disclosed herein further include a handle assembly that is attached to the catheter shaft and that is handled and used by the user or operator to operate, position and control the catheter. In various embodiments, the handle assembly has a source manifold incorporated and/or integrated therein. In such embodiments, the source manifold can include one or more of a manifold housing, a pressure sensor that is coupled to and/or integrated into the manifold housing, and a media inflation port, a guidewire lumen port, an energy guide port, and a catheter shaft port that are formed into and/or coupled to the manifold housing. The pressure sensor is configured to sense a fluid pressure of the catheter fluid within the catheter system. For example, in certain embodiments, the pressure sensor can be configured to sense a fluid pressure within the balloon interior or at any desired location along an inflation conduit. The media inflation port is configured to couple the inflation conduit into and/or through the manifold housing so that the catheter fluid can be directed as desired through the handle assembly and into the balloon interior. The guidewire lumen port is configured to couple a guidewire lumen, which defines a conduit through which a guidewire extends, into, from and/or through the manifold housing, so that the guidewire lumen can thus extend from the handle assembly into and/or through the balloon interior. The energy guide port is configured to couple the one or more energy guides into and/or through the manifold housing, so that the energy guides can guide energy from the energy source, through the handle assembly, and into the balloon interior. The catheter shaft port is configured to couple the catheter shaft to the manifold housing so that the user can effectively control positioning of the catheter shaft, with the balloon attached thereto, substantially adjacent to the vascular lesion(s) at the treatment site via manipulation of the handle assembly.

In some embodiments, the handle assembly can further include at least a portion of a system controller, such as in the form of a printed circuit board (PCB) that is attached to the pressure sensor, and an energy activation button.

The present technology is also directed toward methods for treating a treatment site within or adjacent to a vessel wall, with such methods utilizing the devices disclosed herein.

It should be noted that, as used in this specification and the appended claims, the singular forms "a," "an," and "the" include plural referents unless the content and/or context clearly dictates otherwise. It should also be noted that the term "or" is generally employed in its sense including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

It is recognized that the figures shown and described are not necessarily drawn to scale, and that they are provided for ease of reference and understanding, and for relative positioning of the structures.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of the catheter systems have been illustrated and described herein, one or more features of any one embodiment can be combined with one or more features of one or more of the other embodiments, provided that such combination satisfies the intent of the present invention.

While a number of exemplary aspects and embodiments of the catheter systems have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope, and no limitations are intended to the details of construction or design herein shown.

What is claimed is:

1. A catheter system for use by a user in treating a vascular lesion within or adjacent to a blood vessel within a body of a patient, the catheter system comprising:

a catheter shaft;

a handle assembly that is coupled to the catheter shaft, the handle assembly including an assembly housing, the handle assembly being usable by the user to selectively position the catheter shaft near the vascular lesion; and a source manifold that is positioned substantially within the assembly housing, the source manifold including a manifold housing that is distinct from the assembly housing, the manifold housing having at least three ports formed therein including a catheter shaft port that is configured to receive a portion of the catheter shaft so that the catheter shaft is coupled to the manifold housing, and the at least three ports comprising an energy guide port that is configured to receive a portion of an energy guide and a guidewire lumen port that is transverse to the energy guide port and is configured to receive a portion of a guidewire lumen, wherein the at least three ports are positioned entirely within the assembly housing.

2. The catheter system of claim 1 further comprising a pressure sensor that is coupled to the manifold housing, the pressure sensor being configured to sense a fluid pressure of a catheter fluid within the catheter system.

3. The catheter system of claim 2 wherein the handle assembly further includes circuitry that is electrically coupled to the pressure sensor.

4. The catheter system of claim 3 wherein the circuitry includes a printed circuit board.

5. The catheter system of claim 3 wherein the handle assembly further includes an energy activator that is coupled to the circuitry, the energy activator being configured to activate the catheter system.

6. The catheter system of claim 2 wherein the manifold housing includes a sensor bore, and the pressure sensor is positioned within the sensor bore.

7. The catheter system of claim 1 wherein the manifold housing includes a first housing member and a second housing member that is attachable to the first housing member via an attachment assembly.

8. The catheter system of claim 7 wherein the attachment assembly includes a first attachment member that is coupled to the first housing member and a second attachment member that is coupled to the second housing member, the first attachment member being configured to engage the second attachment member when the first housing member is attached to the second housing member.

9. The catheter system of claim 8 wherein the first attachment member includes an attachment channel, and the second attachment member includes an attachment projection.

10. The catheter system of claim 8 wherein the first attachment member and the second attachment member are attached to one another with an adhesive material.

11. The catheter system of claim 8 wherein the first attachment member and the second attachment member are ultrasonically sealed to one another.

12. The catheter system of claim 1 further comprising a balloon that is coupled to the catheter shaft, the balloon including a balloon wall that defines a balloon interior, the balloon being configured to retain a catheter fluid within the balloon interior.

13. The catheter system of claim 12 further comprising a pressure sensor that is coupled to the manifold housing, the pressure sensor being configured to sense a fluid pressure of the catheter fluid within the balloon interior.

14. The catheter system of claim 12 further comprising an energy guide that is coupled to the source manifold, the energy guide including a guide distal end that is configured to be positioned within the balloon interior, the energy guide is configured to guide energy from an energy source through the energy guide and into the balloon interior to generate a plasma bubble in the catheter fluid.

15. The catheter system of claim 14 wherein the energy guide includes an optical fiber and the energy source includes a laser.

16. The catheter system of 14 wherein the energy guide includes an electrode pair having spaced apart electrodes that extend into the balloon interior, and the energy source is a high voltage energy source that provides pulses of high voltage energy to the energy guide to generate an electrical arc across the electrodes.

17. The catheter system of claim 12 further comprising a guidewire lumen, and an inflation conduit that is configured to guide the catheter fluid into the balloon interior; and wherein the manifold housing includes a media inflation port that receives a portion of the inflation conduit.

18. The catheter system of claim 17 wherein the manifold housing includes a first housing member and a second housing member that are selectively attached to one another; and wherein each of the catheter shaft port, the energy guide port, the guidewire lumen port and the media inflation port are formed into the second housing member.

19. The catheter system of claim 1 wherein the manifold housing is configured to simultaneously guide a guidewire and the energy guide into the catheter shaft.

20. The catheter system of claim 1 wherein the manifold housing has at least four ports formed therein including the catheter shaft port that is configured to receive the portion of the catheter shaft so that the catheter shaft is coupled to the manifold housing, and each of (i) the energy guide port that is configured to receive a portion of an energy guide, (ii) the guidewire lumen port that is configured to receive a portion of a guidewire lumen, and (iii) the media inflation port that is configured to receive a portion of an inflation conduit.

21. A method for treating a vascular lesion within or adjacent to a blood vessel within a body of a patient, the method including the step of providing the catheter system of claim 1.

* * * * *